(12) United States Patent
Takahashi et al.

(10) Patent No.: US 9,808,198 B2
(45) Date of Patent: Nov. 7, 2017

(54) BIOLOGICAL INFORMATION MEASURING DEVICE

(71) Applicant: Seiko Epson Corporation, Tokyo (JP)

(72) Inventors: Yusuke Takahashi, Matsumoto (JP); Hideto Yamashita, Suwa (JP); Akira Inagaki, Matsumoto (JP); Hironori Hasei, Azumino (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/957,299

(22) Filed: Dec. 2, 2015

(65) Prior Publication Data
US 2016/0206215 A1    Jul. 21, 2016

(30) Foreign Application Priority Data

Jan. 20, 2015    (JP) .................................. 2015-008362

(51) Int. Cl.
*A61B 5/0205*    (2006.01)
*A61B 5/00*    (2006.01)
*A61B 5/021*    (2006.01)

(52) U.S. Cl.
CPC .......... *A61B 5/681* (2013.01); *A61B 5/02108* (2013.01); *A61B 5/743* (2013.01); *A61B 2560/0257* (2013.01); *A61B 2562/0219* (2013.01)

(58) Field of Classification Search
None
See application file for complete search history.

(56) References Cited

U.S. PATENT DOCUMENTS

| 8,712,724 | B2 * | 4/2014 | Yuen | A61B 5/0002 |
| | | | | 702/160 |
| 8,744,804 | B2 * | 6/2014 | Messenger | G06Q 30/02 |
| | | | | 702/160 |
| 8,751,194 | B2 * | 6/2014 | Panther | G06F 3/04883 |
| | | | | 702/160 |
| D720,249 | S * | 12/2014 | Park | D11/3 |
| 8,903,671 | B2 * | 12/2014 | Park | G08B 21/18 |
| | | | | 702/104 |
| 8,920,332 | B2 * | 12/2014 | Hong | A61B 5/02427 |
| | | | | 600/309 |
| 2011/0295547 | A1 | 12/2011 | Asada et al. | |

FOREIGN PATENT DOCUMENTS

| JP | 2005-185631 A | 7/2005 |
| WO | WO-2010-089828 A1 | 8/2010 |

* cited by examiner

*Primary Examiner* — Brian T Gedeon
(74) *Attorney, Agent, or Firm* — ALG Intellectual Property, LLC

(57) ABSTRACT

A biological information measuring device includes a case section having, in sectional view, a trapezoidal shape including an upper base and a lower base shorter than the upper base, a first leg substantially orthogonal to the upper base and the lower base, and a second leg that is the opposite side of the first leg, a display section disposed on the second leg side, a main circuit board housed in the case section, a flexible board configured to electrically connect the main circuit board and the display section, and a pulse-wave sensor section disposed on the first leg side and configured to detect a pulse wave signal of a user. The flexible board is disposed on the lower base side.

21 Claims, 20 Drawing Sheets

BIOLOGICAL INFORMATION MEASURING DEVICE

CROSS-REFERENCES TO RELATED APPLICATIONS

This application claims priority to Japanese Patent Application No. 2015-008362, filed Jan. 20, 2015, the entirety of which is hereby incorporated by reference.

BACKGROUND

1. Technical Field

The present invention relates to a biological information measuring device.

2. Related Art

There has been known a portable biological information measuring device worn on the body of a user to measure biological information. The portable biological information measuring device has been spread as a "wearable device" through, for example, improvement of wearability.

For example, JP-A-2005-185631 (Patent Literature 1) introduces a biological information measuring device of a wristwatch type that measures a pulse wave using a pulse wave sensor mounted thereon in a state in which a user wears the biological information measuring device on the arm of the user.

WO 2010/089828 (Patent Literature 2) introduces a biological information measuring device of a wristwatch type or a belt type mounted with an inertial sensor such as an acceleration sensor and worn on the arm or the waist of a user to measure a moving distance, body motions, and the like of the user during exercise such as walking or running.

According to the growing health awareness in recent years, there is an increasing demand for a wearable device have mounted with a plurality of sensors, capable of measuring and detecting a more variety of biological information, position information, and the like, and excellent in wearability and having a high fitting feeling.

However, when it is attempted to give a variety of measuring and detecting functions to the wearable devices, the number of components mounted thereon increases and the devices are increased in size. It is likely that wearability and portability are spoiled. Further, since power consumption increase when functions of the devices increase, it is difficult to measure biological information for a sufficiently long period.

SUMMARY

An advantage of some aspects of the invention is to solve at least a part of the problems described above and provide a biological information measuring device capable of measuring and detecting a variety of biological information without spoiling wearability and portability.

Application Example 1

A biological information measuring device according to this application example includes: a case section having, in sectional view, a trapezoidal shape including an upper base and a lower base shorter than the upper base, a first leg crossing the upper base and the lower base, and a second leg that is the opposite side of the first leg; a display section disposed on the second leg side; a circuit board housed in the case section; a flexible board configured to electrically connect the circuit board and the display section; and a pulse wave sensor disposed on the first leg side and configured to detect a pulse wave signal of a user. The flexible board is disposed on the lower base side.

Note that, in this application example, it is preferable that the first leg and the upper and lower bases cross substantially orthogonally.

It is preferable that the upper base and the lower base are disposed in parallel.

In the case section in this application example having the trapezoidal shape in section, among the four sides of the trapezoid, one bottom side of "bottom sides", which are opposite sides parallel to each other, is referred to as "upper base" and the other bottom side shorter than the upper base is referred to as "lower base". One leg, that is, a "first leg", of "legs", which are opposite sides different from the bottom sides, is substantially orthogonal to the upper base and the lower base. That is, a "second leg", which is the other leg, forms an oblique side that connects an end portion of the "upper base" extending substantially orthogonally from one end of the first leg and an end portion of the "lower base" extending orthogonally from the other end of the first leg.

According to this application example, the display section is disposed on the second leg side that forms the oblique side of the case section having the trapezoidal shape in sectional view, the pulse wave sensor is disposed on the first leg side, which is the opposite side of the second leg, and the circuit board is disposed in a region between the display section and the pulse wave sensor. Therefore, it is possible to efficiently use a housing space in the case section. A connection length of the flexible board may be short.

Therefore, since efficiency of a component housing space in the case section and a reduction in the sizes of components can be realized, it is possible to provide a small and light biological information measuring device.

Application Example 2

In the biological information measuring device according to the application example, the pulse wave sensor may be disposed in a region including the center of gravity of the case section on a surface of the case section on the first leg side.

According to this application example, since a contact position and a contact state of the pulse wave sensor with the body of the user are stabilized, it is possible to improve detection accuracy of the pulse wave signal of the user.

Application Example 3

In the biological information measuring device according to the application example, the pulse wave sensor may be provided on a surface of the case section on the first leg side and disposed in a sensor projecting section projecting to the body side of the user.

According to this application example, since the pulse wave sensor is disposed in the sensor projecting section projecting to the body side of the user, the contact state of the pulse wave sensor with the body of the user is further stabilized. It is possible to further improve the detection accuracy of the pulse wave signal of the user.

Application Example 4

In the biological information measuring device according to the application example, the biological information measuring device may further include a vibration motor housed on the first leg side in the case section in sectional view, and the vibration motor may be disposed further on the upper base side than the center of a surface on the first leg side.

According to this application example, it is possible to dispose the vibration motor, which is a relatively large component, with high space efficiency in a space on the upper base side larger than a space on the lower base side in the case section. Since the vibration motor, which causes vibration during driving, can be disposed apart from the display section, it is possible to suppress aged deterioration of the display section that occurs because the vibration of the vibration motor is continuously applied.

Application Example 5

In the biological information measuring device according to the application example, the biological information measuring device may further include at least one battery housed in the case section, and the battery may be disposed with the center of gravity of the battery located further on the upper base side than the center of a surface on the first leg side.

According to this application example, it is possible to dispose, with increased flexibility of a layout, the battery, which is a particularly large and heavy component in the biological information measuring device, in the space on the upper base side larger than the space on the lower base side in the case section.

Application Example 6

In the biological information measuring device according to the application example, the biological information measuring device may further include a band section configured to fix the case section to an organism, and the band section may include a first band connected to the upper base side, a second band connected to the lower base side, and a connecting section that connects the first band and the second band.

According to this application example, since the first band and the second band are connected by the connecting section, it is possible to wear the case section of the biological information measuring device on the body of the user with satisfactory wearability. Further, it is possible to easily perform attachment and detachment of the biological information measuring device.

Application Example 7

In the biological information measuring device according to the application example, surfaces of the first band and the second band on the organism side and a surface of the case section on the first leg side may form a continuous surface.

According to this application example, the surface of the case section on the first leg side, that is, the surface on the organism side, and the surfaces of the first band and the second band on the organism side are continuous. Therefore, satisfactory wearability is obtained when the case section of the biological information measuring device is worn on the body of the user by the band section including the first band and the second band.

Application Example 8

In the biological information measuring device according to the application example, a surface of the case section on the first leg side may have a curved surface.

According to this application example, the surface of the case section on the first leg side, that is, the surface on the organism side has a curved surface extending along the body of the user on which the biological information measuring device is worn. The surface on the organism side having the curved surface and the surfaces of the first band and the second band on the organism side are continuous. Therefore, more satisfactory wearability (fitting feeling) is obtained when the case section of the biological information measuring device is worn on the body of the user by the band section.

Application Example 9

In the biological information measuring device according to the application example, when the case section is worn on the wrist of the user, the lower base side may be located on the body side of the user.

According to this application example, since the biological information measuring device is worn on the wrist with the lower base side of the case section in sectional view directed to the body of the user, a display surface of the display section is a slope inclining downward from the upper base side to the lower base side. Therefore, there is an effect that the user can easily visually recognize the display section.

Application Example 10

In the biological information measuring device according to the application example, an atmospheric pressure sensor configured to detect the atmospheric pressure may be housed in the case section, and the atmospheric pressure sensor may be disposed not to overlap the pulse wave sensor in plan view.

As the pulse wave sensor mounted on the biological information measuring device, for example, a photoelectric pulse wave sensor including a light source that irradiates light on the organism and a light receiving element that receives reflected light from the organism can be suitably used. According to this application example, since the atmospheric pressure sensor is disposed not to overlap the pulse wave sensor in plan view, the atmospheric pressure sensor is less easily affected by, for example, fluctuation in a flow of the air due to the heat of a light emitting section of the pulse wave sensor. It is possible to more accurately perform the measurement of the atmospheric pressure by the atmospheric pressure sensor. The atmospheric pressure sensor needs to have a hole for introducing the air on the outside of the case section in order to measure the atmospheric pressure. Therefore, a ventilation hole is essential in the vicinity of the atmospheric pressure sensor of the case section. However, if the atmospheric pressure sensor is disposed near a pulse meter, it is likely that external light intrudes into the case inside from the ventilation hole and adversely affects the measurement of the pulse wave sensor. On the other hand, by adopting the configuration of this application example, it is possible to prevent the intrusion of the external light into the pulse wave sensor. Therefore, there is an effect that measurement accuracy of the pulse wave sensor is stabilized.

Application Example 11

In the biological information measuring device according to the application example, the atmospheric pressure sensor and the pulse wave sensor may be respectively disposed on different surfaces of the circuit board.

According to this application example, since the atmospheric pressure sensor and the pulse wave sensor are disposed on the different surfaces of the same circuit board, it is possible to reduce the number of components and attain a reduction in the size and a reduction in the thickness of the biological information measuring device. Further, there is an effect that an adverse effect on the measurement of the pulse wave sensor is suppressed.

Application Example 12

In the biological information measuring device according to the application example, the circuit board may include a main circuit board mounted with at least the atmospheric pressure sensor and a sensor circuit board separate from the main circuit board and mounted with the pulse wave sensor.

According to this application example, since the circuit board separately includes the main circuit board mounted with at least the atmospheric pressure sensor and the sensor circuit board mounted with the pulse wave sensor, it is possible to increase flexibility of a layout of detecting sections such as the pulse wave sensor and the atmospheric pressure sensor in the case section.

Application Example 13

In the biological information measuring device according to the application example, a hole section that causes the atmospheric pressure sensor and the external air to communicate with each other may be provided in a region in an extending direction to the second leg side of the sensor projecting section of the case section.

In the configuration in which the atmospheric pressure sensor is housed in the case section of the biological information measuring device, the hole section that causes the space in the case section, in which the atmospheric pressure sensor is housed, and the external air to communicate with each other needs to be provided in the case section. According to this application example, the hole section for the atmospheric pressure sensor is provided in the region in the extending direction on the second leg side of the sensor projecting section of the case section. Consequently, when stress is applied to the case section worn on the body of the user, durability against the stress is increased by a rib structure formed by the sensor projecting section. Therefore, it is possible to reduce the influence of deterioration in strength due to the hole section provided in the case section.

Application Example 14

In the biological information measuring device according to the application example, the vibration motor may be mounted on a surface of the circuit board on the same side as the pulse wave sensor.

According to this application example, since the vibration motor is mounted on the surface on the same organism side as the pulse wave sensor on the circuit board, the vibration motor is disposed in the case section with high space efficiency. This can contribute to a reduction in size. Further, it is possible to make it easy for the user to sense notification of information by the vibration of the vibration motor.

Application Example 15

In the biological information measuring device according to the application example, the biological information measuring device may further include a temperature sensor housed in the case section and configured to detect the temperature of an organism, and the temperature sensor may be mounted on a surface of the circuit board on the same side as the pulse wave sensor.

According to this application example, since the temperature sensor is mounted on the surface on the same organism side as the pulse wave sensor on the circuit board, the temperature sensor is disposed in the case section with high space efficiency. This can contribute to a reduction in size. Further, it is possible to more surely perform measurement of the body temperature of the user by the temperature sensor.

Application Example 16

In the biological information measuring device according to the application example, the case section may house a position calculating section configured to calculate position information on the basis of a positioning signal from a positioning satellite and a first antenna configured to acquire the positioning signal, and the first antenna may be disposed on the lower base side.

A state suitable as a wearing state of the biological information measuring device in this application example is a state in which the lower base side is located on the body side of the user when the biological information measuring device is worn on the wrist with the lower base side of the case section of the biological information measuring device directed to the body of the user. According to this application example, in a state of the posture of the user wearing the biological information measuring device on the wrist, the first antenna is often located upward in the vertical direction. Therefore, it is possible to suitably receive a signal for positioning with the first antenna.

Application Example 17

In the biological information measuring device according to the application example, the case section may house a second antenna configured to communicate biological information with an external device, and the second antenna may be disposed on the lower base side in sectional view.

According to this application example, in a state of the posture of the user wearing the biological information measuring device on the wrist, the second antenna is often located upward in the vertical direction. Therefore, when the user communicates using the second antenna while wearing the biological information measuring device on the wrist, it is possible to perform satisfactory communication.

Application Example 18

In the biological information measuring device according to the application example, at least one of the first antenna and the second antenna may be disposed in the vicinity of the hole section.

According to this application example, in communication with the outside performed using at least one of the first antenna and the second antenna, the sensitivity of transmission and reception is improved from the sensitivity in communication performed via the outer wall of the case section. Therefore, it is possible to perform satisfactory communication.

Application Example 19

In the biological information measuring device according to the application example, an inertial sensor or an inertial sensor section including a plurality of kinds of the inertial sensors may be provided in the case section, and the inertial sensor or the inertial sensor section may be disposed in a region including the center of gravity of the case section in plan view.

According to this application example, an inertial sensor section including a plurality of kinds of inertial sensors such as an acceleration sensor and an angular velocity sensor (a gyro sensor) or one inertial sensor is disposed in a position where the inertial sensor section or the inertial sensor is more stable than when the inertial sensor section or the inertial sensor is disposed in the vicinity of an end portion of the device in plan view. Therefore, it is possible to improve measurement accuracy by the inertial sensor.

Application Example 20

In the biological information measuring device according to the application example, the inertial sensor may be disposed not to overlap the vibration motor in plan view.

According to this application example, since the inertial sensor such as the acceleration sensor or the angular velocity sensor is disposed in the position not overlapping the vibration motor in plan view, the inertial sensor is less easily affected by noise of the vibration motor. It is possible to perform stable measurement of inertia with the inertial sensor.

Application Example 21

In the biological information measuring device according to the application example, the pulse wave sensor may be a photoelectric pulse wave sensor including a light source configured to irradiate light on the body of the user and a light receiving element configured to receive reflected light from the body of the user, a light blocking member may be disposed between the pulse wave sensor and a surface that is in contact with the organism, and a first optical waveguide configured to optically connect the light source and the surface that is in contact with the organism and a second optical waveguide configured to optically connect the light receiving element and the surface that is in contact with the organism may be provided in the light blocking member.

According to this application example, the first optical waveguide that optically connects the light source and the surface that is in contact with the organism and the second optical waveguide that optically connects the light receiving element and the surface that is in contact with the organism are disposed via the light blocking member. Consequently, illumination light irradiated on the organism from the light source and reflected light received by the light receiving element from the organism are optically blocked by the light blocking member. Therefore, it is possible to efficiently irradiate the illumination light from the light source on the organism. Further, it is possible to efficiently receive, with the light receiving element, the reflected light from the organism based on the illumination light.

Therefore, it is possible to provide the biological information measuring device including the pulse wave sensor that realizes more accurate pulse wave detection.

BRIEF DESCRIPTION OF THE DRAWINGS

The invention will be described with reference to the accompanying drawings, wherein like numbers reference like elements.

DESCRIPTION OF EXEMPLARY EMBODIMENTS

Embodiments of the invention are explained below with reference to the drawings. Note that, in the figures referred to below, layers and members are sometimes shown in scales different from actual scales in order to show the layers and the members in recognizable sizes.

First Embodiment

Figure 1A:
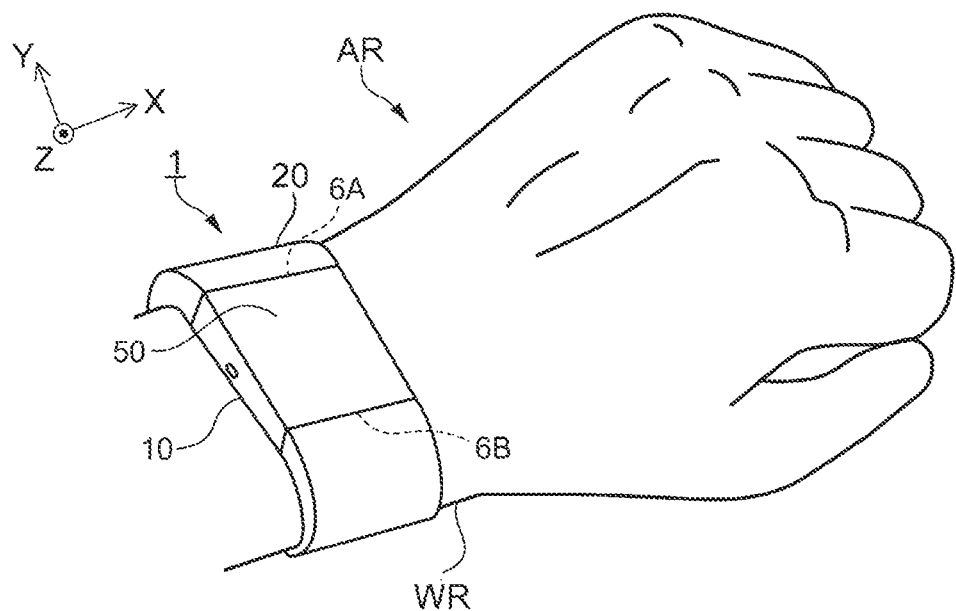
FIG. 1A is an explanatory diagram showing a wearing state in which a biological information measuring device according to the first embodiment is worn on an organism.
Figure 1B:
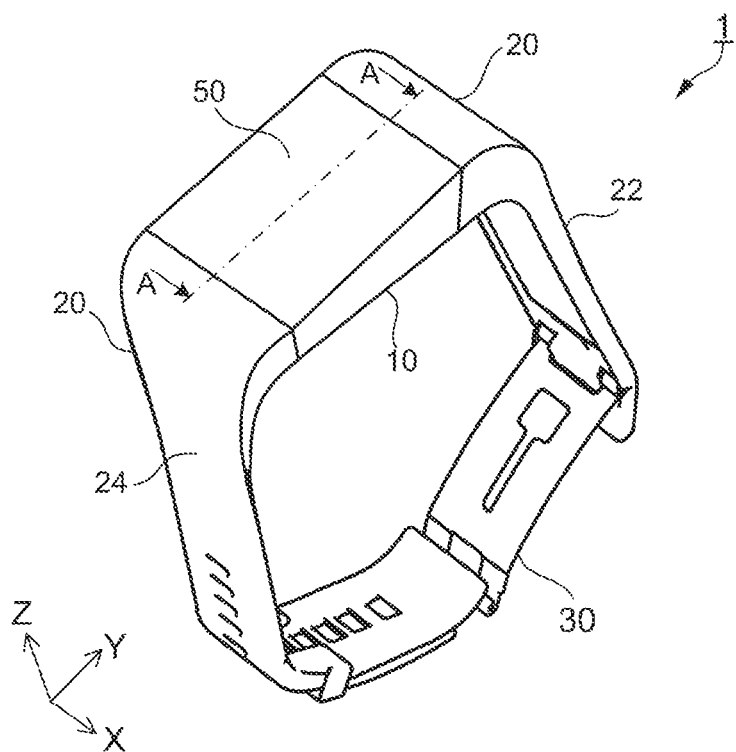
FIG. 1B is a perspective view showing an open state in which the biological information measuring device is detached from the organism.

FIG. 1A is an explanatory diagram showing a wearing state in which a biological information measuring device according to a first embodiment is worn on an organism. FIG. 1B is a perspective view showing an open state in which the biological information measuring device is detached from the organism.

First, the schematic configuration of a biological information measuring device 1 according to the first embodiment is explained.

In FIGS. 1A and 1B, the biological information measuring device (hereinafter also referred to as measuring device) according to the first embodiment is an electronic device worn on an organism (e.g., a human body), biological information of which is measured, to measure a pulse and other biological information. The measuring device 1 in the first embodiment is worn on a measurement part of a user (the organism) like a wristwatch and used.

In this specification, the normal direction of the front surface of the measuring device 1 is represented as a Z-axis direction positive on the front side in FIG. 1A. Note that details of the definition of the Z-axis direction are explained below. The front surface of the measuring device 1 indicates a surface on which a display section 50 is disposed. A direction crossing the Z-axis direction, that is, the length direction of an arm AR is represented as an X-direction positive in a distal end side on which the fingers are present. A direction crossing the Z-axis direction and the X-axis direction, that is, the width direction of the arm AR, is represented as a Y-axis direction positive on the little finger side.

In this specification, viewing the measuring device 1 from the normal direction of the front surface (the Z-axis direction) is referred to as "front view". Viewing the measuring device 1 from the X-axis direction is referred to as "side view". In a state in which the measuring device 1 is worn on a wrist WR, the organism side, that is, aside facing the wrist WR is referred to as "inner side" or "inner surface" and the opposite side of the organism, that is, the opposite side of the side facing the wrist WR is referred to as "outer side" or "outer surface". Note that viewing the cross section of the measuring device 1 viewed from a direction same as the "side view", that is, an A-A line section of FIG. 1B is referred to as "sectional view". In this specification, the sectional view is a particularly important illustration direction. In the following explanation, the sectional view is often explained in detail.

As shown in FIG. 1B, the measuring device 1 includes a case section 10, which is a device main body, a band section 20 including a first band 22 and a second band 24 that fix the case section 10 to the wrist WR, and a buckle section 30 functioning as a connecting section that connects the first band 22 and the second band 24 of the band section 20.

On the front surface side of the case section 10, the display section (a monitor section (a display)) 50 that displays a biological information measurement result, time, and the like as characters, graphics, and the like is provided. The measuring device 1 measures biological information in a state in which the bottom surface (a detecting section) on the opposite side of the front surface of the measuring device 1 is closely attached to the wrist WR. The measuring device 1 displays, on the display section 50, a measurement result, an evaluation result of the biological information based on the measurement result, and the like.

In the band section 20, the first band 22 is extended from one side (specifically, a "upper base" 6A side described later) of the case section 10, the second band 24 is extended from the other side (specifically, a "lower base" 6B side described later) of the case section 10, the distal end sides of the first band 22 and the second band 24 are coupled to each other by the buckle section 30. The buckle section 30 in this embodiment is a hinge-like member obtained by connecting two metal plates with a turning shaft. The buckle section 30 is structured to be reduced in length when the two plates are folded to overlap each other and to be increased in length when the two plates are extended in line. That is, the measuring device 1 includes the case section 10 including the detecting section that detects biological information, the band section 20 for fixing the case section 10 to an organism, and the buckle section 30 annularly connected to the band section 20 and capable of adjusting the length of the band section 20.

Both end portions of the band section 20 (end portions of the first band 22 and the second band 24) are coupled by the buckle section 30 in this way. Consequently, the measuring device 1 has an annular shape in both of a state in which the measuring device 1 is worn on the wrist WR (hereinafter referred to as wearing state) shown in FIG. 1A and a state in which the measuring device 1 is detached from the wrist WR (hereinafter referred to as open state) shown in FIG. 1B.

With this configuration, when the user wears the measuring device 1, the user can wear the measuring device 1 as shown in FIG. 1A by extending the buckle section 30 and, after narrowing and inserting the hand into an annular large opening shown in FIG. 1B, folding and shortening the buckle section 30 in a wearing position of the arm. In particular, by applying various original ideas such as optimization of the configuration and the material of the band section 20 and the size of the annular opening, a configuration is realized in which, even if the measuring device 1 is repeatedly attached and detached, the detecting section such as a pulse-wave sensor section 5 explained below can be fixed in a detecting position of the arm accurately and with substantially the same pressing (a pressing force).

Note that, in this embodiment, the measuring device 1 of a type worn by the band section 20 and the folding-type buckle section 30 is explained. However, it is also possible to use a band and a connecting section of a type including a clasp and a prong on one end side of a band section and a small hole in a stitch of the band section on the other end side to insert the stitch on the other end side through the clasp and put the prong into the small hole and fix the prong.

Figure 2A:
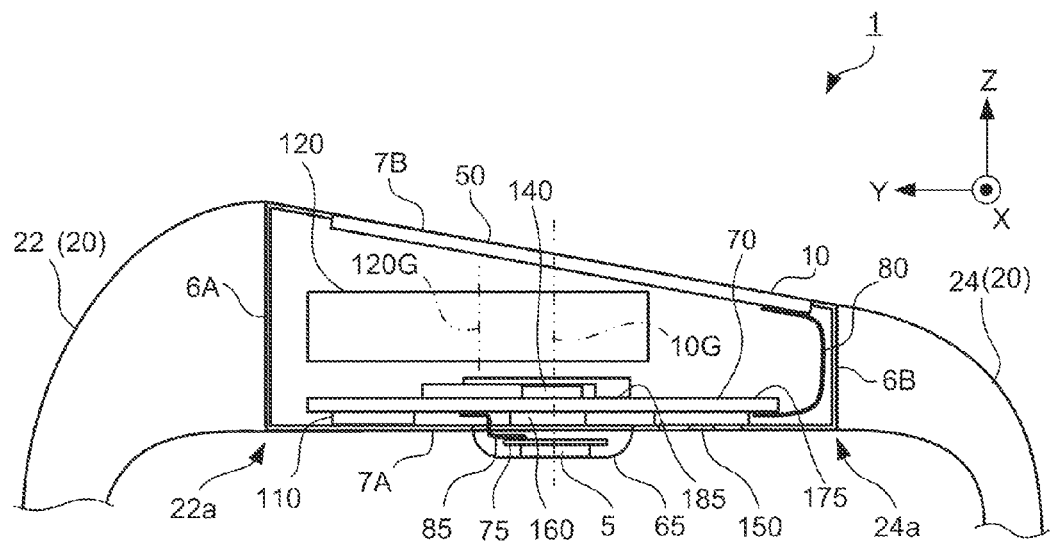
FIG. 2A is an A-A line sectional view of FIG. 1B showing the schematic configuration of the biological information measuring device according to the first embodiment.
Figure 2B:
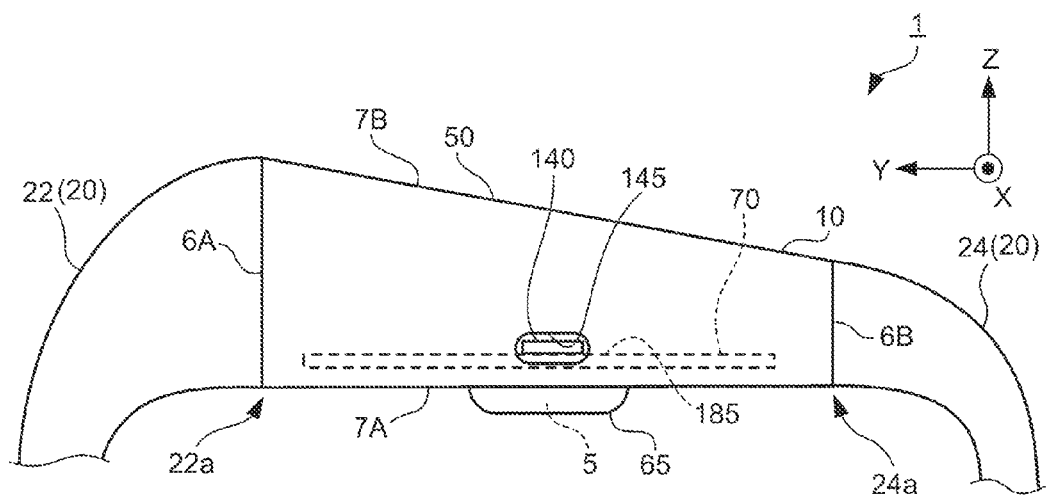
FIG. 2B is a side view showing an exterior viewed from a direction same as a direction in FIG. 2A.

Details of the configuration of the biological information measuring device 1 are explained with reference to the drawings. FIGS. 2A and 2B show the schematic configuration of the biological information measuring device according to the first embodiment. FIG. 2A is an A-A line sectional view of FIG. 1B. FIG. 2B is a side view showing an exterior viewed from a direction same as a direction in FIG. 2A.

As shown in FIG. 2A, in the biological information measuring device 1 in this embodiment, the case section 10 has a trapezoidal shape in sectional view. In a trapezoid, opposite sides parallel to each other are called "bases", one of the bases is called "upper base" and the other is called "lower base", and the other opposite sides different from the bases are called "legs". The case section 10 in this embodiment having a trapezoidal shape in sectional view has an upper base 6A, which is one side (a longer side) of the bases, a lower base 6B, which is the other side shorter than the upper base 6A, a first leg 7A, which is one leg substantially orthogonal to the upper base 6A and the lower base 6B, and a second leg 7B, which is the opposite side of the first leg 7A (the other leg). The second leg 7B forms, in the case section 10 having the trapezoidal shape in sectional view, an oblique side connecting an end portion of the longer upper base 6A extending from one end of the first leg 7A in a substantially orthogonal direction and an end portion of the shorter lower base 6B extending from the other end of the first leg 7A in a substantially orthogonal direction. In other words, the upper base 6A and the lower base 6B are disposed substantially in parallel. The first leg 7A and the second leg 7B are not disposed in parallel and are disposed to form a predetermined angle. Alternatively, an angle formed by the upper base 6A and the first leg 7A in sectional view can be considered larger than an angle formed by the upper base 6A and the second leg 7B. An angle formed by the lower base 6B and the first leg 7A can be considered smaller than an angle formed by the lower base 6B and the second leg 7B. Further, the angle formed by the second leg 7B and the upper base 6A can be considered smaller than the angle formed by the second leg 7B and the lower base 6B. By adopting the asymmetrical sectional structure or the structure having asymmetrical capacities with respect to the center of the case, it is possible to secure design flexibility, designability, and visibility. Note that the case section 10 is made of a resin material such as polycarbonate (PC), polystyrene (PS), or ABS resin.

In the display section 50 disposed on a surface on the second leg 7B side that forms the oblique side as explained above, when the biological information measuring device 1 is worn with a surface on the first leg 7A side thereof directly or indirectly set in contact with the skin of the wrist (an organism) of the user, a display surface of the display section 50 forms a slope. As shown in FIG. 1A, the biological information measuring device 1 in this embodiment is worn in a direction in which the lower base 6B side of the case section 10 is located on the body side of the user. Consequently, the display surface of the display section 50 forms a slope inclining downward from the upper base 6A side to the lower base 6B side (the body side of the user). Therefore, there is an effect that the user can easily visually recognize display on the display section 50. Note that, as explained above, in this specification, the normal direction of the front surface of the measuring device 1 is represented as the Z direction positive on the front side in FIG. 1A. However, as explained above, since the display section 50 inclines in the measuring device 1, the normal line of the surface on the first leg 7A side in the sectional view may be defined as the Z axis.

Referring back to FIG. 2A, in the case section 10, on the first leg 7A side in sectional view, a main circuit board 70 mounted with main driving and control circuits of the biological information measuring device 1 including a driving circuit of the display section 50, a biological-information detecting section explained below, and the like is disposed. The detailed configuration of the main circuit board 70 is explained below. The main circuit board 70 and the display section 50 are electrically connected by a flexible board (hereinafter referred to as FPC (Flexible Printed circuit)) 80 on the lower base 6B side. The length between the main circuit board 70 and the display section 50 is smaller on the lower base 6B side than on the upper base 6A side. Therefore, a connection length of the main circuit board 70 and the display section 50 by the FPC 80 may be small. A reduction in the size of a component (the FPC 80) can be attained. This is advantageous for a reduction in the size of the biological information measuring device 1.

On the first leg 7A side of the case section 10, that is, the organism side (the wrist side) of the user, the pulse-wave sensor section 5 that detects a pulse wave serving as biological information is disposed. In this embodiment, a sensor projecting section 65 projecting to the organism side of the user is formed on the surface of the case section 10 on the first leg 7A side. The pulse-wave sensor section 5 is mounted on a sensor circuit board 75 disposed in an internal space of the sensor projecting section 65. The sensor circuit board 75 is electrically connected to the main circuit board 70 via a relay board 85 such as an FPC. The sensor projecting section 65 can be a rib formed integrally with the case section 10.

In this way, the pulse-wave sensor section 5 is disposed in the sensor projecting section 65 projecting to the organism side of the user. Consequently, a contact state of the pulse wave sensor with the body of the user is stabilized. There is an effect of improving detection accuracy of a pulse wave signal. The pulse-wave sensor section 5 is disposed in a region including a center of gravity 10G of the case section 10 on the surface of the case section 10 on the first leg 7A side. With this configuration, a contact position and a contact state of the pulse-wave sensor section 5 with the organism (the wrist) of the user are stabilized. Detection accuracy of a pulse wave signal can be improved. In the biological information measuring device 1 in this embodiment, the sensor circuit board 75 mounted with the pulse-wave sensor section 5 is provided separately from the main circuit board 70 mounted with the main driving and control circuits and various detecting sections explained below. Consequently, in the biological information measuring device 1 requested to be reduced in size, it is possible to realize improvement of flexibility of a layout of the pulse-wave sensor section 5 and the other various detecting sections in the case section 10.

Figure 3:
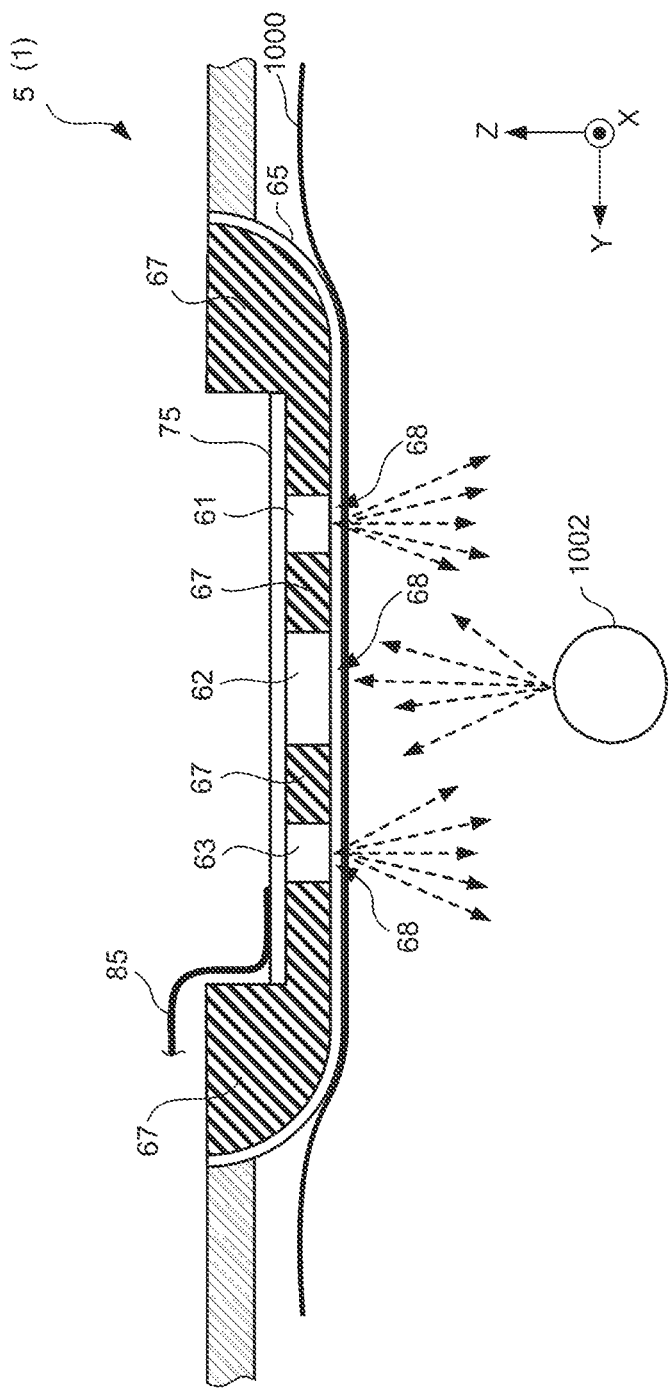
FIG. 3 is a partial sectional view schematically showing the schematic configuration and a measurement principle of a pulse-wave sensor section.

The configuration and a measurement principle of the pulse-wave sensor section 5 are explained. FIG. 3 is a partial sectional view schematically showing the schematic configuration and the measurement principle of the pulse-wave sensor section 5. In FIG. 3, the pulse-wave sensor section 5 is a photoelectric pulse wave sensor including the sensor circuit board 75 disposed in the sensor projecting section 65 and light emitting elements 61 and 63 (usually, LEDs (Light emitting Diodes) are used) functioning as light sources and a light receiving element 62 (usually, a photodiode is used) mounted on the surface of the sensor circuit board 75 on the organism (skin 1000 of the wrist) side of the user. Inside the sensor projecting section 65, the light emitting elements 61 and 63 and the light receiving element 62 are blocked by light blocking members 67. Window sections 68 of the light emitting element 61 and the light receiving element 62 on the skin 1000 side have light transmittance. The window sections 68 are transparent convex lens-like members. Transparent resin is suitably used. Light irradiated on the skin (the organism) 1000 of the user from the light emitting elements 61 and 63 of the pulse-wave sensor section 5 through the window sections 68 is partially absorbed by blood flowing in a blood vessel 1002 under the skin 1000. However, the remaining light is reflected to the outside from the skin 1000. The light reflected by the organism is captured by the light receiving element 62 and output to the main circuit board 70 (see FIGS. 2A and 2B) via the relay board 85 as a light reception signal. The light reception signal from the light receiving element 62 is a signal including information equivalent to a blood amount flowing in the blood vessel. The blood amount flowing in the blood vessel changes according to the pulsation of the heart. Therefore, the signal of the light receiving element 62 changes to correspond to the beat of the heart. That is, the change in the signal of the light receiving element 62 is equivalent to a pulse of a heart rate. A heart rate per one minute of the heart is obtained by counting the number of pulses per unit time (e.g., per 10 seconds).

Referring back to FIGS. 2A and 2B, the case section 10 including the pulse-wave sensor section 5 disposed in the sensor projecting section 65 is worn on the wrist of the user by the band section 20 including the first band 22 connected to the upper base 6A side of the case section 10 and the second band 24 connected to the lower base 6B side of the case section 10. That is, in the side view shown in FIG. 2B, the band section 20 assumes a reverse U-shape in which, from the sensor projecting section 65 in the top disposed in a region (a region substantially in the center) including the center of gravity 10G of the case section 10, the first band 22 and the second band 24 hang down to both sides (the left and right on the paper surface of the figures) of the sensor projecting section 65 (see FIG. 1B as well). The surface of the first band 22 on the organism side (the first leg 7A side) and the surface of the case section 10 on the organism side smoothly continue in a boundary portion 22a. The surface of the second band 24 on the organism side and the surface of the case section 10 on the organism side smoothly continue in a boundary portion 24a. Consequently, with the band section 20 including the first band 22 and the second band 24, satisfactory wearability is obtained when the case section 10 of the biological information measuring device 1 is worn on the body of the user. The position and a contact state of the pulse-wave sensor section 5 on the organism of the user are stabilized. Therefore, it is possible to obtain an accurate pulse wave measurement result.

Note that, as the material of the band section 20, for example, silicone rubber, natural rubber, isoprene rubber, butadiene rubber, styrene-butadiene rubber, chloroprene rubber, nitrile rubber, polyisobutylene, ethylene propylene rubber, chlorosulfonated polyethylene rubber, acrylic rubber, fluorine rubber, epichlorohydrin rubber, urethane rubber, styrene-based elastomer, olefin-based elastomer, vinyl chloride-based elastomer, polyester-based elastomer, polyurethane-based elastomer, silicone-based elastomer, amide-based elastomer, nylon-based elastomer, dynamically cross-linked elastomer, and the like or a blend of the forgoing can be used. The band section 20 desirably has elasticity and satisfactory durability for obtaining a proper binding force on the wrist WR and is mild for skin (has fewer stimuli to skin). As a material having such characteristics, silicone rubber can be suitably used.

In the case section 10, a battery 120, which is a power supply of the biological information measuring device 1, is housed. In this embodiment, one battery 120 is disposed between the display section 50 and the main circuit board 70 with a center of gravity 120G of the battery 120 located further on the upper base 6A side than the center of gravity 10G of the surface of the case section 10 on the first leg 7A side in sectional view. With this configuration, it is possible to adopt a battery having a large capacity without depending on the size on the lower base 6B side. The battery, which is a particularly large and heavy component in the biological information measuring device, can be disposed in a space on the upper base side larger than a space on the lower base side in the case section 10. Therefore, it is possible to increase flexibility of a layout. Further, there is an effect that a weight balance of the case section 10 is stabilized.

Figure 4A:
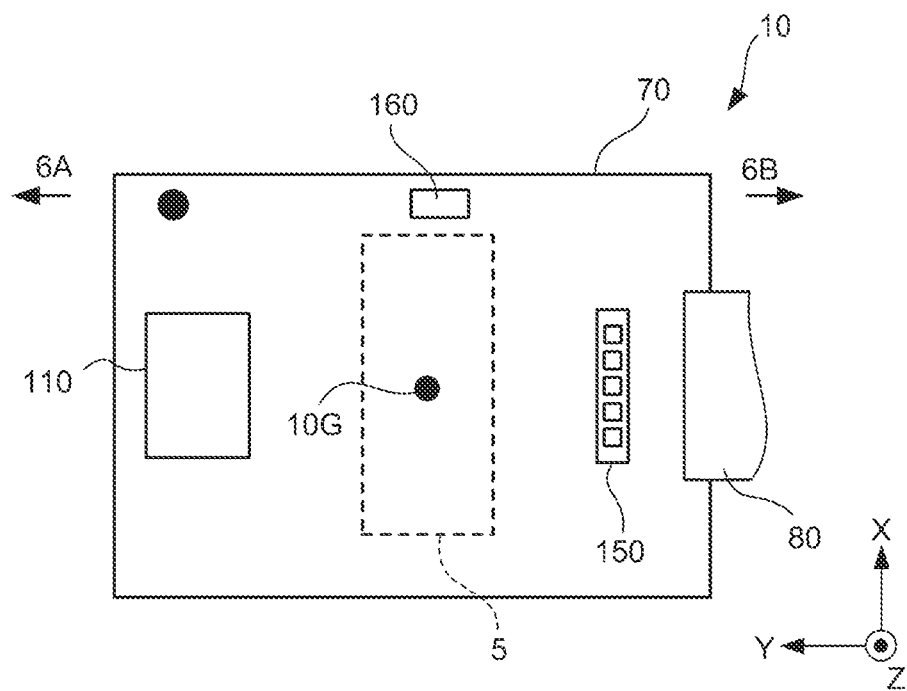
FIG. 4A is a schematic plan view schematically showing the configuration on one surface of a main circuit board.
Figure 4B:
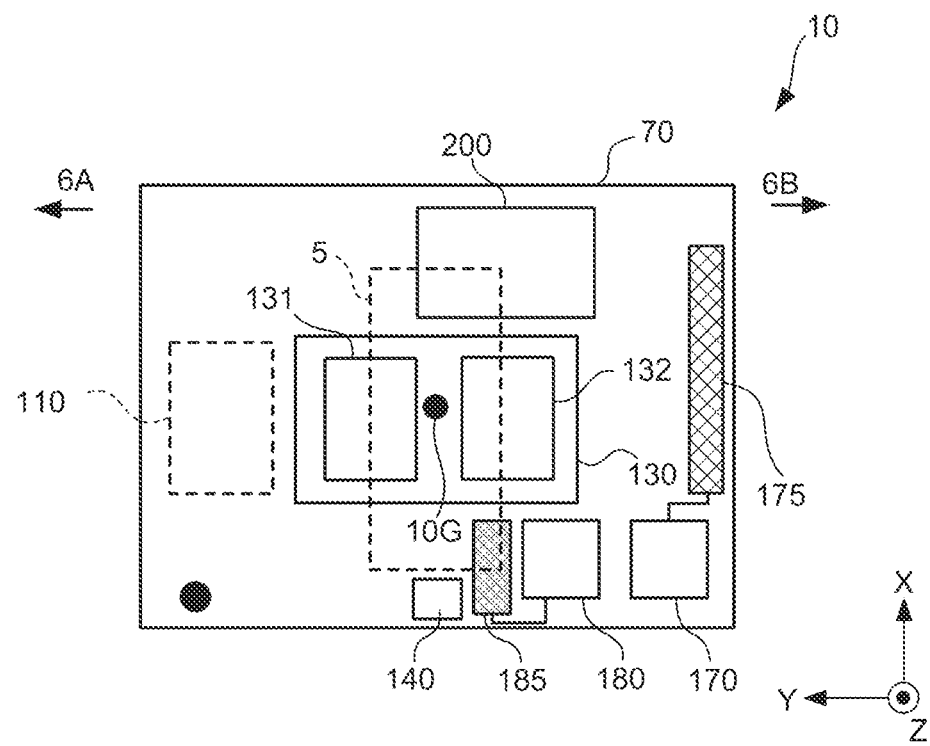
FIG. 4B is a schematic plan view schematically showing the configuration of the other surface of the main circuit board.

The various detecting sections (measuring sections) included in the biological information measuring device 1 in this embodiment besides the pulse-wave sensor section 5 are explained. FIGS. 4A and 4B are diagrams schematically showing the main circuit board 70 mounted with the various detecting sections and the like. FIG. 4A is a schematic plan view showing the configuration on one surface of the main circuit board 70. FIG. 4B is a schematic plan view showing the configuration on the other surface of the main circuit board 70.

One surface of the main circuit board 70 shown in FIG. 4A is a surface on the pulse-wave sensor section 5 side in FIGS. 2A and 2B, that is, a surface on the organism side of the user (the first leg 7A side). A vibration motor 110 and a temperature sensor 160 are mounted on one surface (the lower surface) of the main circuit board 70.

The vibration motor 110 transmits, to the user, with vibration, information such as a determination result of a state of the user based on a measurement result of biological information or the like by the biological information measuring device 1. As shown in FIG. 2A, the vibration motor 110 is disposed further on the upper base 6A side than the center (in the figure, the center of gravity 10G) of the surface of the case section 10 on the first leg 7A side. With this configuration, the vibration motor 110, which is a relatively large component, can be efficiently disposed in a space on the upper base 6A side larger than a space on the lower base 6B side in the case section 10. The vibration motor 110, which causes vibration during driving, can be disposed further apart from the display section 50 than when the vibration motor 110 is disposed on the lower base 6B side. Therefore, aged deterioration of the display section 50 can be suppressed. Further, in this embodiment, the vibration motor 110 is disposed on a surface on the same organism side as the pulse-wave sensor section 5 of the main circuit board 70. Consequently, it is possible to make it easy for the user to sense notification of information by the vibration of the vibration motor 110.

The temperature sensor 160 detects the temperature of the user (the organism), that is, a body temperature. Since the temperature sensor 160 is disposed on the surface on the same organism side as the pulse-wave sensor section 5 of the main circuit board 70 as explained above, it is possible to more surely perform the measurement of the body temperature of the user by the temperature sensor 160. Note that the temperature sensor 160 can also measure an environmental temperature.

On one surface of the main circuit board 70, a charging terminal section 150 for charging the battery 120 (see FIG. 2A) is provided.

The other surface of the main circuit board 70 shown in FIG. 4B is a surface on the display section 50 side (the second leg 7B side) in FIGS. 2A and 2B. On the other surface (the upper surface) of the main circuit board 70, an inertial sensor section 130 and an atmospheric pressure sensor 140 functioning as detecting sections (measuring sections) and a GPS (Global Positioning System) unit 170 functioning as a position calculating section are mounted.

The inertial sensor section 130 includes at least one inertial sensor. The inertial sensor section 130 in this embodiment includes an acceleration sensor 131 and an angular velocity sensor (a gyro sensor) 132. The acceleration sensor 131 detects respective accelerations in three axial directions crossing (ideally, orthogonal) to one another and outputs a digital signal (acceleration data) corresponding to the magnitudes and the directions of the detected three-axis accelerations. The angular velocity sensor 132 detects respective angular velocities in three axial directions crossing (ideally, orthogonal) to one another and outputs a digital signal (angular velocity data) corresponding to the magnitudes and the directions of the detected three-axis angular velocities.

The inertial sensor section 130 is disposed in a region including the center of gravity 10G of the case section 10 in plan view. Since the inertial sensor section 130 including the acceleration sensor 131 and the angular velocity sensor 132 is disposed in the region including the center of gravity 10G of the case section 10 in this way, the inertial sensor section 130 is disposed in a position where a posture is more stabilized than when the inertial sensor section 130 is disposed in the vicinity of an end portion of the case section 10 (the measuring device 1). Therefore, there is an effect that measurement accuracy of inertia by the inertial sensors such as the acceleration sensor 131 and the angular velocity sensor 132 is improved. The acceleration sensor 131 and the angular velocity sensor 132 of the inertial sensor section 130 are disposed in positions not overlapping the vibration motor 110, which is disposed on one surface of the main circuit board 70, in plan view. The inertial sensors such as the acceleration sensor 131 and the angular velocity sensor 132 are disposed in the positions not overlapping (positions apart from) the vibration motor 110 in plan view in this way. Therefore, the inertial sensors are less easily affected by noise of the vibration motor 110. It is possible to perform stable measurement of inertia by the acceleration sensor 131 and the angular velocity sensor 132.

Note that the signals from the acceleration sensor 131 and the angular velocity sensor 132 of the inertial sensor section 130 can also be used in, when biological information is detected, for example, processing for suppressing body motion noise superimposed on a pulse wave signal detected by the pulse-wave sensor section 5.

The atmospheric pressure sensor 140 detects the atmospheric pressure of a space where the user wearing the biological information measuring device 1 is present. The atmospheric pressure sensor 140 is disposed not to overlap the pulse-wave sensor section 5 in plan view. Consequently, the atmospheric pressure sensor 140 is less easily affected by, for example, fluctuation in a flow of the air due to the heat of a light emitting section of the pulse-wave sensor section 5 of a photoelectric type. It is possible to more accurately perform the measurement of the atmospheric pressure by the atmospheric pressure sensor 140. As in this embodiment, the atmospheric pressure sensor 140 and the pulse-wave sensor section 5 including the sensor circuit board 75 are disposed on the different surfaces of the main circuit board 70. Consequently, since the space of the main circuit board 70 can be efficiently utilized, there is an effect of attaining a reduction in the size and the thickness of the biological information measuring device 1.

As shown in FIG. 2B, in the case section 10, a hole section 145 that causes the internal space of the case section 10 and the outdoor air to communicate with each other is provided. The atmospheric pressure sensor 140 is disposed in the vicinity of the hole section 145. The hole section 145 is provided in a region in an extending direction to the second leg 7B side of the sensor projecting section 65 of the case section 10. Consequently, in the region in the extending direction to the second leg 7B side of the sensor projecting section 65 of the case section 10, deformation due to stress applied when the case section 10 is worn on the body of the user is suppressed by a rib structure formed by the sensor projecting section 65. Therefore, it is possible to reduce the influence of deterioration in strength due to the hole section 145 provided in the case section 10.

The GPS unit 170 receives a GPS satellite signal transmitted from a GPS satellite, which is a type of a positioning satellite, performs positioning calculation using the GPS satellite signal to calculate the position and the speed (a vector including magnitude and a direction) of the user, and outputs GPS data obtained by adding time information and positioning accuracy information to the position and the speed of the user. Note that a method of calculating a position and speed using a GPS and a method of generating time information using the GPS are publicly known. Therefore, detailed explanation of the methods is omitted.

On the main circuit board 70, a GPS antenna 175 functioning as a first antenna electrically connected to the GPS unit 170 to receive a positioning signal from a positioning satellite is disposed. The GPS antenna 175 is disposed on the lower base 6B side in the case section 10. With this configuration, the distance to an upper part of the case section 10, that is, the second leg 7B side (the display section 50) is shorter than when the GPS antenna 175 is disposed on the upper base 6A side of the main circuit board 70 (see FIG. 2A). Therefore, there is an effect that reception sensitivity of the positioning signal from the positioning satellite is increased and satisfactory positioning is performed. Note that the GPS antenna 175 may be printed on the outer side of the flexible board 80 or may be disposed on a board separate from the main circuit board 70. In both the configurations, the GPS satellite 175 only has to be disposed on the lower base 6B side in the case section 10.

Besides, a control section 200 and a communication section 180 are disposed on the other surface of the main circuit board 70. The control section 200 is configured by, for example, a CPU, a ROM, and a RAM not shown in the figure. These kinds of hardware and software stored in the ROM or the like cooperate with each other to control the operation of the biological information measuring device 1.

The communication section 180 performs wireless communication between the biological information measuring device 1 and an external device such as a smart phone or a personal computer according to a publicly-known wireless communication system such as Bluetooth (registered trademark). Consequently, it is possible to operate the measuring device 1 from the external device, transmit biological information of a wearer measured by the measuring device 1 to the external device, and accumulate and manage the biological information of the wearer. The measuring device 1 has a function of, in cooperation with the external device, accumulating the measured biological information of the wearer and providing, on the basis of the information, the user with information concerning, for example, whether an analysis result of the biological information and an exercise amount is proper. A second antenna 185 connected to the communication section 180 to communicate the biological information and the like with the external device is disposed on the other surface of the main circuit board 70. As shown in FIG. 2B, the second antenna 185 in this embodiment is disposed in the vicinity of the hole section 145 of the case section 10. With this configuration, in the communication with the outside performed using the second antenna 185, the sensitivity of transmission and reception of a signal is improved from communication performed via the outer wall of the case section 10. Therefore, it is possible to perform satisfactory communication. Note that it goes without saying that the effect of improving the communication sensitivity by disposing the antenna in the vicinity of the hole section 145 is also effective for the GPS antenna 175 functioning as the first antenna. Like the GPS antenna 175, the second antenna 185 may be disposed on the main circuit board 70 on the lower base 6B side in the sectional view of the case 10. In that case, it is possible to enjoy an effect that satisfactory communication can be performed because the distance between the second antenna 185 and the surface of the case section 10 on the second leg 7B side (the surface of the display section 50) decreases.

As explained above, with the biological information measuring device 1 according to this embodiment, the case section 10, in which the various detecting sections are housed, has, in sectional view, a trapezoidal shape formed by the upper base 6A and the lower base 6B shorter than the upper base 6A, the first leg 7A substantially orthogonal to the upper base 6A and the lower base 6B, and the second leg 7B, which is the opposite side of the first leg 7A. The main circuit board 70 is housed in the case section 10. The display section 50 is disposed on the second leg 7B side of the case section 10. The main circuit board 70 and the display section 50 are electrically connected via the FPC 80 on the lower base 6B side. Relatively large electronic components such as detecting sections (detecting devices) are disposed in a space on the upper base 6A side that forms a relatively wide space in the case section 10.

With this configuration, it is possible to dispose various electronic components and the like with high space efficiency effectively making use of the space in the case section 10. The main circuit board 70 and the display section 50 are electrically connected via the FPC 80 on the lower base 6B side where a connection length may be small. Consequently, it is possible to efficiently use the housing space in the case section 10. A connection length by the FPC 80 may be small. Therefore, since efficiency of the component housing space in the case section 10 and a reduction in the sizes of the components can be realized, it is possible to provide a small and light biological information measuring device.

Note that the invention is not limited to the embodiment explained above. Various changes, improvements, and the like can be added to the embodiment. Modifications are explained below.

Modifications

Figure 5A:
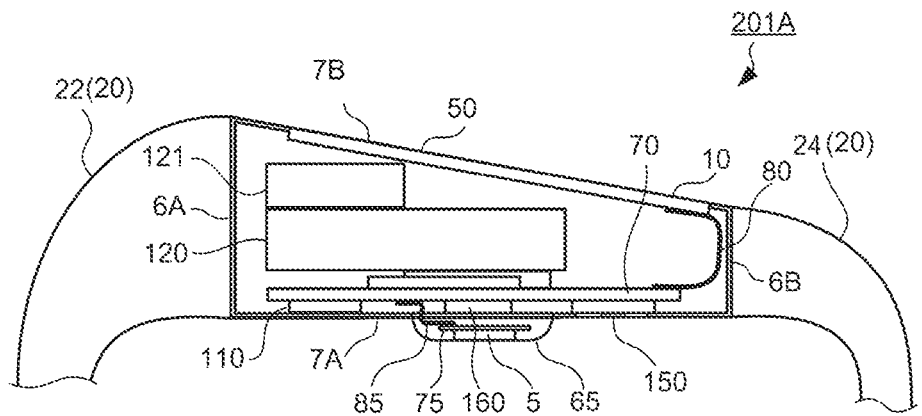
FIGS. 5A to 5C are schematic sectional views respectively showing variations of a layout configuration in a case section.
Figure 5B:
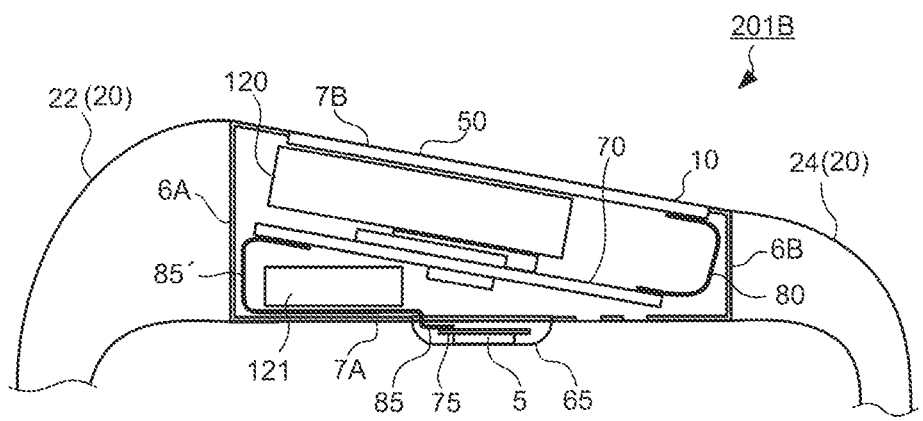
Figure 5C:
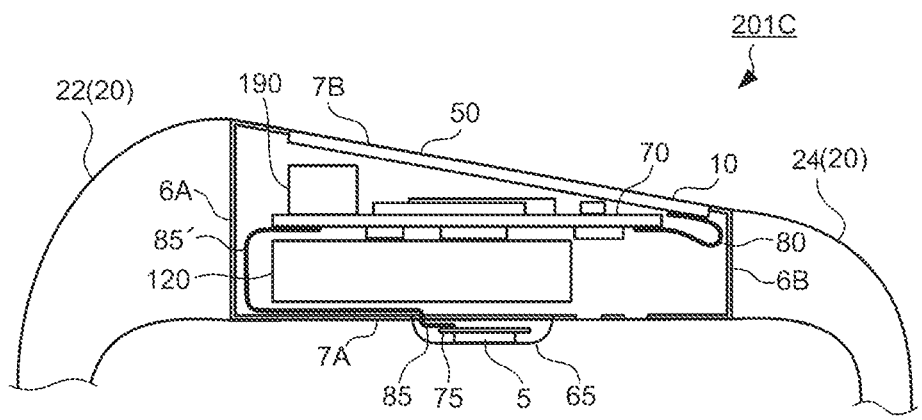

FIGS. 5A to 5C are modifications of the first embodiment and are schematic sectional views respectively showing variations of a layout configuration in a case section of a biological information measuring device.

In the first embodiment, the configuration is explained in which, as shown in FIGS. 2A and 2B, the one battery 120 is disposed between the main circuit board 70 and the display section 50 in the space in the case section 10 of the biological information measuring device 1. However, the case section 10 is not limited to this configuration. Variations of the layout configuration in the case section 10 in a biological information measuring device according to the modification are explained below. Note that components same as the components in the first embodiment are denoted by the same reference numerals and signs and redundant explanation of the components is omitted.

In a biological information measuring device 201A shown in FIG. 5A, a first variation of the layout configuration in the case section 10 is shown. In the biological information measuring device 201A, in the case section 10, together with the battery 120 having specifications same as the specifications in the first embodiment, a second battery 121 having a size smaller than the battery 120 is disposed above the main circuit board 70 disposed in a layout same as the layout in the first embodiment. The second battery 121 is disposed on the upper base 6A side on the battery 120 in the sectional view of the case section 10. With this configuration, it is possible to realize an efficient layout making use of a relatively wide space on the upper base 6A side in the case section 10 and secure a power supply having electric power larger than electric power in the first embodiment without increasing the size of the case section 10.

In a biological information measuring device 201B shown in FIG. 5B, a second variation of the layout configuration in the case section 10 is shown. In the biological information measuring device 201B, in the case section 10, the main circuit board 70 disposed in a layout same as the layout in the first embodiment and the battery 120 disposed in a position close to the upper base 6A above the main circuit board 70 are obliquely disposed in a state in which the side on the upper base 6A side is turned upward (to the display section 50 side) with a turning axis set in the length direction of a side of the main circuit board 70 on the lower base 6B side. In this modification, respective principal planes of the main circuit board 70 and the battery 120 are disposed substantially in parallel to the display surface of the display section 50 that forms the slope of the case section 10. The second battery 121 is disposed in a space in a lower part (the first leg 7A side) on the upper base 6A side of the main circuit board 70 formed by obliquely disposing the main circuit board 70 as explained above. The sensor circuit board 75 mounted with the pulse-wave sensor section 5 and the obliquely disposed main circuit board 70 are electrically connected via a relay board 85' lightly longer than the relay board 85 (see FIGS. 2A and 2B) in the first embodiment.

With this configuration, it is possible to secure, effectively making use of the relatively wide space on the upper base 6A side in the case section 10, a power supply having larger electric power than the electric power in the first embodiment without increasing the size of the case section 10.

FIG. 5C shows a biological information measuring device 201C by a third variation of the layout configuration in the case section 10. In the biological information measuring device 201C, the battery 120 is disposed close to the upper base 6A side on the first leg 7A side in the case section 10. The main circuit board 70 is disposed above (the display section 50 side) of the battery 120. A detecting section 190 for biological information and the like different from the various detecting sections (measuring sections) explained above can be disposed in a relatively wide space formed on the upper base 6A side above the main circuit board 70. Note that a second battery or the like can also be disposed instead of the detecting section 190. With such a configuration, it is possible to give a detecting function anew and secure, effectively making use of the relatively wide space on the upper base 6A side in the case section 10, a power supply having large electric power without increasing the size of the case section 10.

Like the biological information measuring devices 201A to 201C in the modifications explained above, in the biological information measuring device according to the invention, large electronic components and the like can be disposed with increased flexibility of a layout by using the relatively wide space formed on the upper base 6A side in the sectional view of the case section 10.

Second Embodiment

Figure 6:
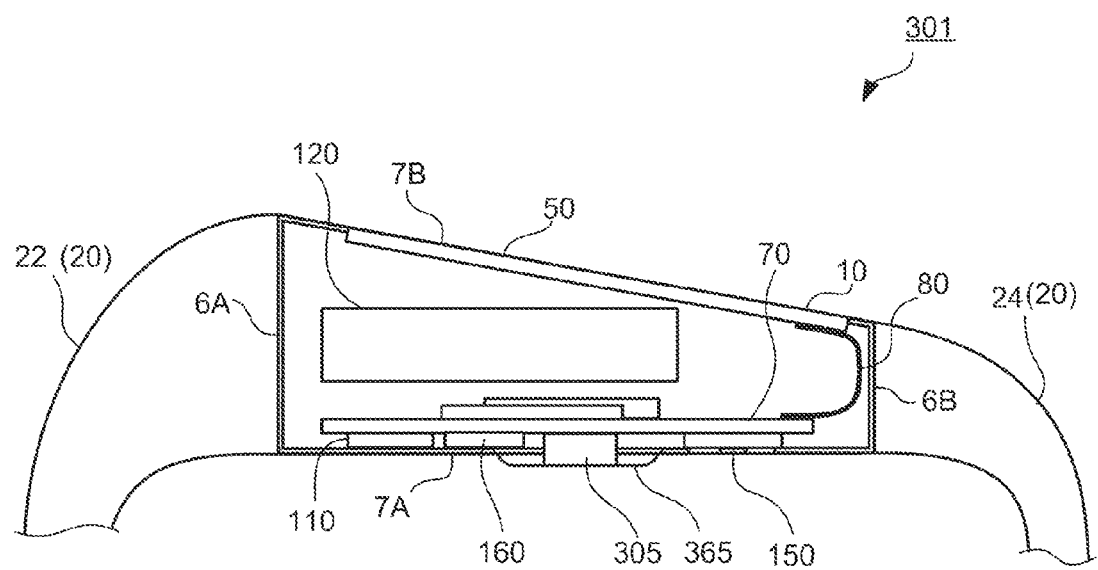
FIG. 6 is a sectional view showing the schematic configuration of a biological information measuring device according to a second embodiment.

FIG. 6 is a sectional view showing the schematic configuration of a biological information measuring device according to a second embodiment.

A biological information measuring device 301 according to the second embodiment is explained with reference to FIG. 6. Note that components same as the components in the first embodiment are denoted by the same reference numerals and signs and redundant explanation of the components is omitted.

In the first embodiment, the configuration (see FIGS. 2A and 2B) is explained in which the pulse-wave sensor section 5 is mounted on the sensor circuit board 75 separate from the main circuit board 70 and the sensor circuit board 75 and the main circuit board 70 are electrically connected by the relay board 85. However, the configuration of the biological information measuring device according to the invention is not limited to this. In FIG. 6, in the biological information measuring device 301 according to the second embodiment, the main circuit board 70 is disposed on the first leg 7A side in the case section 10. On the first leg 7A side of the case section 10, a sensor projecting section 365 projecting to the organism side (the wrist side) when the biological information measuring device 301 is worn on the wrist of the user is formed. In the sensor projecting section 365, a pulse-wave sensor section 305 mounted on the surface of the main circuit board on the first leg 7A side is disposed. With this configuration, a sensor circuit board exclusive for the pulse-wave sensor section 5 is unnecessary. The number of components can be reduced. The thickness of the case section 10 can be reduced.

In the biological information measuring device 301 in the second embodiment, the vibration motor 110 and the temperature sensor 160 are mounted on the surface of the main circuit board 70 on the same first leg 7A side as the pulse-wave sensor section 305. With this configuration, the vibration motor 110 and the temperature sensor 160 are disposed with high space efficiency in the case section 10 together with the pulse-wave sensor section 305. This can contribute to a reduction in size. The vibration motor 110 is disposed in a direction same as the direction of the pulse-wave sensor section 305 (the sensor projecting section 365) closely attached to the organism side of the user. Therefore, it is possible to cause the user to surely sense notification of information by the vibration of the vibration motor 110. Further, the temperature sensor 160 is satisfactorily disposed on the body of the user. Therefore, it is possible to perform stable measurement of a body temperature.

Note that, although not shown in the figure, a member functioning as a column may be disposed between the surface of the main circuit board 70 on the first leg 7A side and the surface (the inner bottom surface) on the first leg 7A side in the case section 10 to substantially horizontally support the posture of the main circuit board 70.

Third Embodiment

Figure 7:
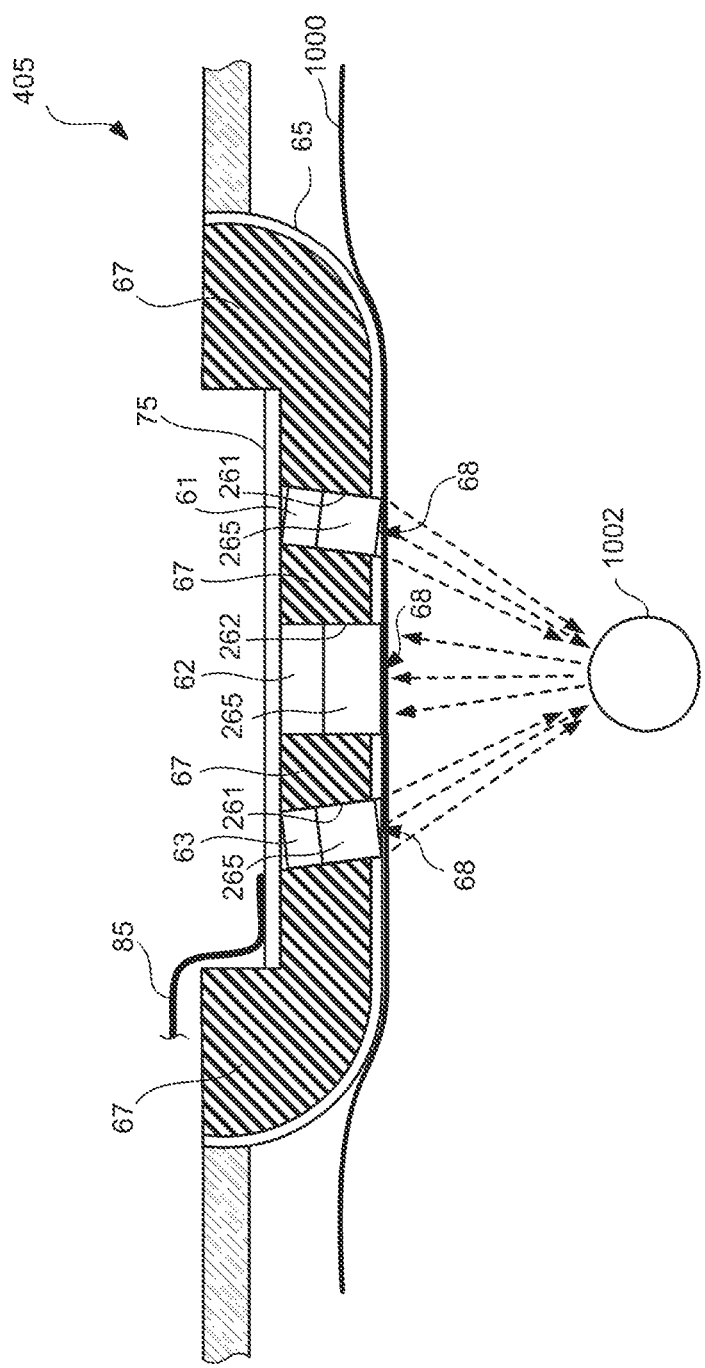
FIG. 7 is a partial sectional view schematically showing the schematic configuration of a pulse-wave sensor section according to a third embodiment.

FIG. 7 is a partial sectional view schematically showing the schematic configuration of a pulse-wave sensor section according to a third embodiment.

A pulse-wave sensor section 405 of a biological information measuring device 401 according to the third embodiment is explained below with reference to FIG. 7. Note that components same as the components in the embodiments explained above are denoted by the same reference numerals and signs and redundant explanation of the components is omitted.

As shown in FIG. 7, the pulse-wave sensor section 405 according to the third embodiment includes the sensor circuit board 75 disposed in the sensor projecting section 65 and the light emitting elements (the LEDs) 61 and 63 and the light receiving element (the photodiode) 62 mounted on the surface of the sensor circuit board 75 on the organism (the skin 1000 of the wrist) side of the user. The light emitting elements 61 and 63 and the light receiving element 62 are blocked by the light blocking members 67. The transparent convex lens-like window sections 68 are disposed on the skin 1000 side of the light emitting elements 61 and 63 and the light receiving element 62. First optical waveguides 261 that optically connect the light emitting elements 61 and 63 to the window sections 68 and a second optical waveguide 262 that optically connects the window section 68 and the light receiving element 62 are formed between the light emitting elements 61 and 63 and the window sections 68. Light transmitting members 265 are embedded in the first optical waveguides 261 and the second optical waveguide 262. As the light transmitting members 265, for example, an optical fiber is suitably used.

With this configuration, the first optical waveguides 261 that optically connect the light emitting elements 61 and 63 and the surface (the window sections 68) that is in contact with the skin 1000 of the organism and the second optical waveguide 262 that optically connects the light receiving element 62 and the surface (the window section 68) that is in contact with the skin 1000 of the organism are disposed via the light blocking members 67. Consequently, illumination lights irradiated on the organism from the light emitting elements 61 and 63 and reflected light received by the light receiving element 62 from the organism are optically blocked by the light blocking members 67. Therefore, it is possible to efficiently irradiate the illumination lights from the light-emitting elements 61 and 63 on the organism. Further, it is possible to efficiently receive, with the light receiving element 62, the reflected light from the organism based on the illumination lights. Therefore, it is possible to provide the biological information measuring device including the pulse-wave sensor section 405 that realizes more accurate pulse wave detection.

In the pulse-wave sensor section 405 shown in FIG. 7, the light emitting elements 61 and 63 and the first optical waveguides 261 provided in parallel on both side across the light receiving element 62 and the second optical waveguide 262 are respectively disposed while being tilted by a predetermined amount toward extended lines extended from the second optical waveguide 262 to the inside of the organism (the skin 1000) of the user. Consequently, lights from the light emitting elements 61 and 63 are concentratedly irradiated on an extended line extended from the light receiving element 62 toward the inside of the inside of the organism of the user. Therefore, since the reflected light from the organism received by the light receiving element 62 is intensified, it is possible to obtain a more accurate pulse wave detection (measurement) value.

Fourth Embodiment

Figure 8:
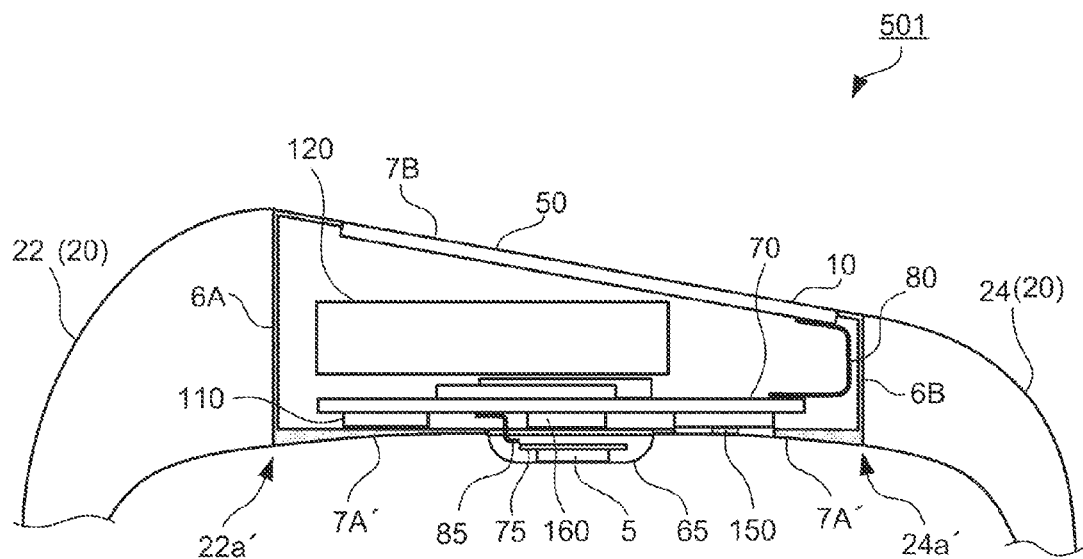
FIG. 8 is a sectional view showing the schematic configuration of a biological information measuring device according to a fourth embodiment.

FIG. 8 is a sectional view showing the schematic configuration of a biological information measuring device according to a fourth embodiment. A biological information measuring device 501 according to the fourth embodiment is explained below with reference to FIG. 8. Note that components same as the components in the embodiments explained above are denoted by the same reference numerals and signs and redundant explanation of the components is omitted.

In FIG. 8, in the biological information measuring device 501 according to the fourth embodiment, a surface of the case section 10 on a first leg 7A' side has a curved surface.

Specifically, the surface on the first leg 7A' side assumes an arch-like shape curving to the display section 50 side from the upper base 6A side toward the center and curving from the center side toward the lower base 6B side to return to the organism side (the opposite side of the display section 50 side). The band section 20 assumes a reverse U-shape in which, from the sensor projecting section 65 in the top disposed in a region substantially in the center of the case section 10, the first band 22 and the second band 24 continue to the curved surface of the surface on the first leg 7A' side of the case section 10 on both sides (the left and right on the paper surface of the figure). The surface of the first band 22 on the organism side (the first leg 7A' side) and the surface of the case section 10 on the organism side and the surface of the second band 24 on the organism side and the surface of the case section 10 on the organism side smoothly continue in respective boundary portions 22a' and 24a' of the surfaces.

According to this embodiment, the surface of the case section 10 on the first leg 7A' side, that is, the surface on the organism side has a curved surface extending along the shape of the organism (the wrist). The surface on the organism side (the surface on the first leg 7A' side) having the curved surface and the surfaces of the first band 22 and the second band 24 on the organism side continue to draw an arc extending along the wrist. Therefore, when the case section 10 of the biological information measuring device 501 is worn on the body of the user by the band section 20, more satisfactory wearability (fitting feeling) is obtained. The position and a contact state of the pulse-wave sensor section 5 including the sensor projecting section 65 with respect to the organism of the user are stabilized. Therefore, there is an effect that a more accurate pulse wave measurement result is obtained.

Fifth Embodiment

A fifth embodiment of the invention is explained below with reference to the drawings.

The pulse-wave sensor section 405 shown in FIG. 7 is illustrated in the embodiment explained above. However, the pulse-wave sensor section according to the invention is not limited to this. A pulse wave sensor illustrated in this embodiment can also be applied.

As in the embodiments explained above, a biological information measuring device (hereinafter referred to as measuring device) according to the fifth embodiment is a heart rate monitoring device worn on an organism (e.g., a human body), biological information of which is measured, to measure biological information such as a pulse (a heart rate). Note that, in figures referred to below, dimensions and ratios of components are sometimes varied from those of actual components as appropriate to show the components in sizes recognizable on the drawings.

First, before explaining the heart rate monitoring device functioning as the biological information measuring device according to the fifth embodiment, an existing example of the heart rate monitoring device functioning as the biological information measuring device according to the fifth embodiment is explained with reference to FIG. 9.

Figure 9:
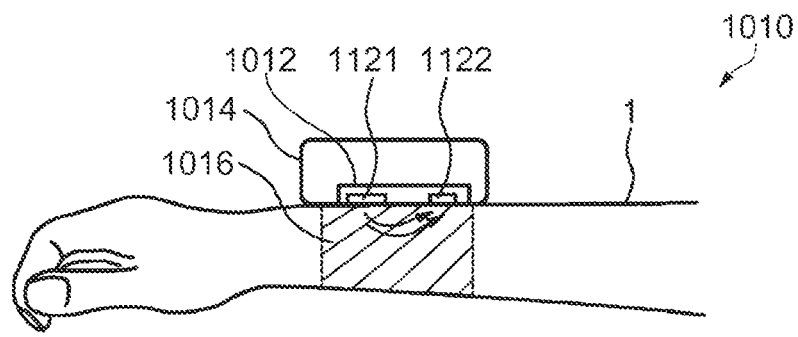
FIG. 9 is a sectional view showing an existing example of a biological information measuring device according to a fifth embodiment.

FIG. 9 is a sectional view showing a heart rate monitoring device 1010 functioning as the biological information measuring device of the existing example that measures physiological parameters of a user having the heart rate monitoring device (in FIG. 9, the arm of the user is shown). The heart rate monitoring device 1010 includes a sensor 1012 that measures a heart rate serving as at least one physiological parameter of the user and a case 1014 that houses the sensor 1012. The heart rate monitoring device 1010 is worn on an arm 1001 of the user by a fixing section 1016 (e.g., a band).

The sensor 1012 is a heart-rate monitoring sensor including a light emitting element 1121 and a light receiving element 1122, which are two sensor elements, to measure or monitor a heart rate. However, the sensor 1012 may be a sensor that measures one or more physiological parameters (e.g., a heart rate, a blood pressure, an expiration amount, skin conductivity, and skin humidity). When the case 1014 includes a housing of a band type, for example, the case 1014 can be used as, for example, a wristwatch-type monitoring device used in sports. Note that the shape of the case 1014 may be any shape as long as the case 1014 can hold the sensor 1012 in a desired position mainly with respect to the user. The case 1014 may be able to optionally house further elements such as a battery, a processing unit, a display, and a user interface.

The biological information measuring device of the existing example is the heart rate monitoring device 1010 for monitoring the heart rate of the user. The sensor 1012 is an optical sensor including the light emitting element 1121 and the light receiving element 1122. The principle of an optical heart rate monitor depends on the light emitting element 1121 (usually, an LED is used) functioning as a light source that irradiates light on skin. The light irradiated on the skin is partially absorbed by blood flowing in a blood vessel under the skin. However, the remaining light is reflected to the outside from the skin. The reflected light is captured by the light receiving element 1122 (usually, a photodiode is used). A light reception signal from the light receiving element 1122 is a signal including information equivalent to a blood amount flowing in the blood vessel. The blood amount flowing in the blood vessel changes according to the pulsation of the heart. In this way, the signal of the light receiving element 1122 changes to correspond to the beat of the heart. That is, the change in the signal of the light receiving element 1122 is equivalent to a pulse of a heart rate. The number of beats of the heart in one minute (i.e., a heart rate) is obtained by counting the number of pulses per unit time (e.g., per 10 seconds).

Figure 10:
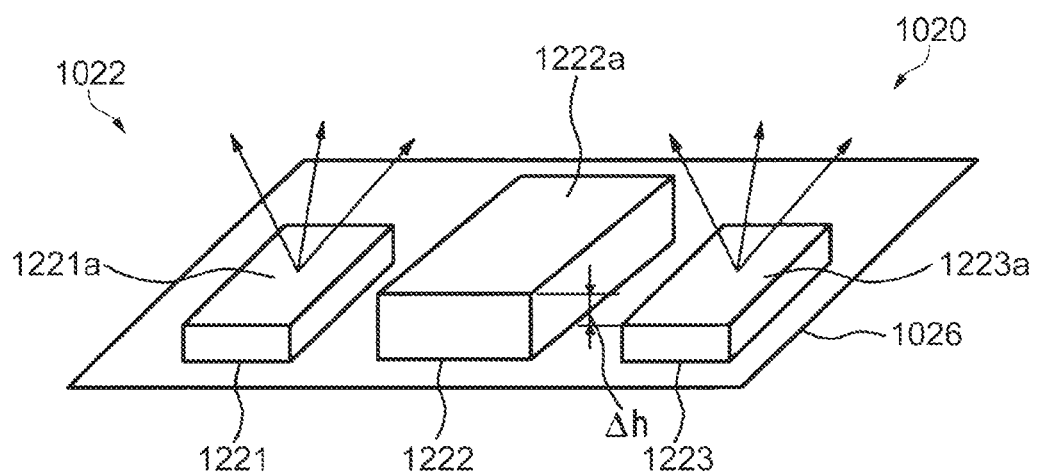
FIG. 10 is a perspective view showing the biological information measuring device according to the fifth embodiment.

A heart rate monitoring device 1020 functioning as a biological information measuring device according to the fifth embodiment is explained with reference to FIG. 10. FIG. 10 is a perspective view showing the heart rate monitoring device functioning as the biological information measuring device according to the fifth embodiment.

The heart rate monitoring device 1020 functioning as the biological information measuring device according to the fifth embodiment includes a sensor 1022 including at least two sensor elements (in this example, includes, as three sensor elements, two light emitting elements 1221 and 1223 functioning as a first light emitting section and a second light emitting section and a light receiving element 1222 functioning as a light receiving section). The sensor elements detect a sensor signal. The sensor 1022 includes an optical sensor including the light emitting elements 1221 and 1223, in which two LEDs for emitting lights to the skin of the user are used, and at least one light receiving element 1222 (a photodiode) for receiving light reflected from the skin. Further, the heart rate monitoring device 1020 includes a case or a housing (not shown in the figure). The case or the housing may be similar to or the same as the case 1014 shown in FIG. 9 or may be similar to or the same as the case section 10 in the first and second embodiments.

The sensor 1022 is born on the entire surface of a carrier (a board) 1026. Lights emitted from the light-emitting elements 1221 and 1223 are reflected without being absorbed by the skin or the like and can directly reach the light receiving element 1222. In the heart rate monitoring device 1020, the distance between the carrier 1026 and upper surfaces 1221a and 1223a of the light emitting elements 1221 and 1223 is smaller than the distance between the carrier 1026 and an upper surface 1222a of the light receiving element 1222. That is, a difference between the distance between the carrier 1026 and the upper surfaces 1221a and 1223a of the light emitting elements 1221 and 1223 and the distance between the carrier 1026 and the upper surface 1222a of the light receiving element 1222 is Δh. The light receiving element 1222 receives light from the upper surface 1222a thereof, which is the top surface layer. With this configuration, there is an effect that most of lights emitted from the light emitting elements 1221 and 1223 travel to the skin and reflected light is directly made incident on the light receiving element 1222 without the intervention of an air layer or the like. In other words, in this structure, since the light receiving element 1222 is closely attached to the skin, it is possible to prevent a gap from being easily formed between the upper surface (a light receiving surface) 1222a of the light receiving element 1222 and the skin. Consequently, it is possible to suppress light acting as a noise source such as external light from being made incident on the upper surface 1222a. Lights from the light emitting elements 1221 and 1223 not passing through the skin, for example, lights directly made incident on the light receiving element 1222 from the light emitting elements 1221 and 1223 cannot reach the upper surface 1222a of the light receiving element 1222.

Sixth Embodiment

Figure 11:
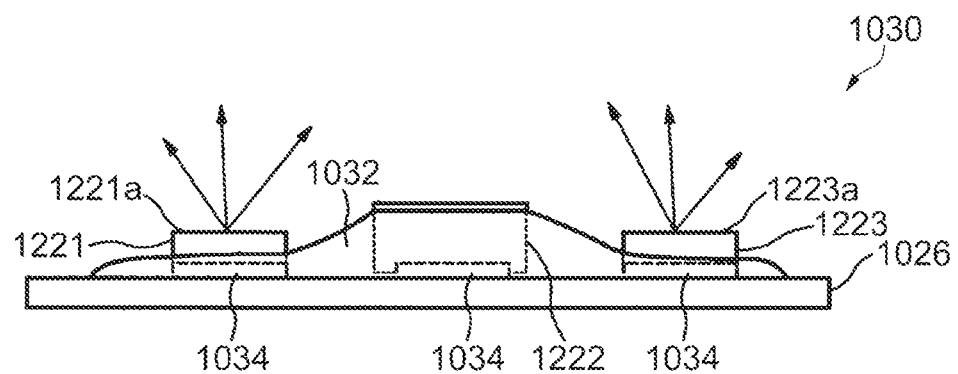
FIG. 11 is a front view showing a biological information measuring device according to a sixth embodiment.

A biological information measuring device 1030 according to a sixth embodiment is explained with reference to FIG. 11. FIG. 11 is a front view showing the biological information measuring device 1030 according to the sixth embodiment. As shown in FIG. 11, electric connection terminals 1034 of the light emitting elements 1221 and 1223 and the light receiving element 1222 have to be desirably covered with an insulative material (e.g., epoxy resin) 1032 to protect electric elements. The insulative material 1032 can be configured not to cover the light emitting elements 1221 and 1223 and the light receiving element 1222. Specifically, a region between the light emitting element 1221 and the light receiving element 1222 and a region between the light emitting element 1223 and the light receiving element 1222 can be configured to be filled with the insulative material 1032. In other words, at least the upper surface 1222a of the light receiving element 1222 and the upper surfaces 1221a and 1223a of the light emitting elements 1221 and 1223 can be configured not to be covered with the insulative material 1032. With such a configuration, it is possible to suppress interference due to air gaps between the skin and the light emitting elements 1221 and 1223. Further, the insulative material 1032 may be configured to cover the upper surfaces 1221a and 1223a of the light emitting elements 1221 and 1223 and the upper surface 1222a of the light receiving element 1222. With such a configuration, it is possible to protect the upper surface 1222a of the light receiving element 1222 and the upper surfaces 1221a and 1223a of the light emitting elements 1221 and 1223 that are in contact with the skin. Therefore, it is possible to prevent damage to the upper surface 1222a of the light receiving element 1222 and the upper surfaces 1221a and 1223a of the light emitting elements 1221 and 1223. In this case, the insulative material 1032 can also be regarded as a protection film.

In the biological information measuring device 1030 according to the sixth embodiment, as a generally possible example, the insulative material 1032 formed of epoxy resin is provided. In FIG. 11, the insulative material 1032 is disposed not to cover the upper surfaces 1221a and 1223a of the light emitting elements 1221 and 1223 and protects the electric connection terminals 1034. Lights emitted from the light emitting elements 1221 and 1223 are represented by arrows.

In this way, the insulative material 1032 is minimally disposed not to prevent correct functions of the biological information measuring device 1030 to thereby protect the electric connection terminals 1034 of the light emitting elements 1221 and 1223 and the light receiving element 1222. Consequently, the biological information measuring device 1030 can be further improved. Note that, instead of the configuration in which epoxy is injected in the sixth embodiment, it is suitable to adopt a biological information measuring device 1040 according to a seventh embodiment shown in FIG. 12.

Seventh Embodiment

Figure 12:
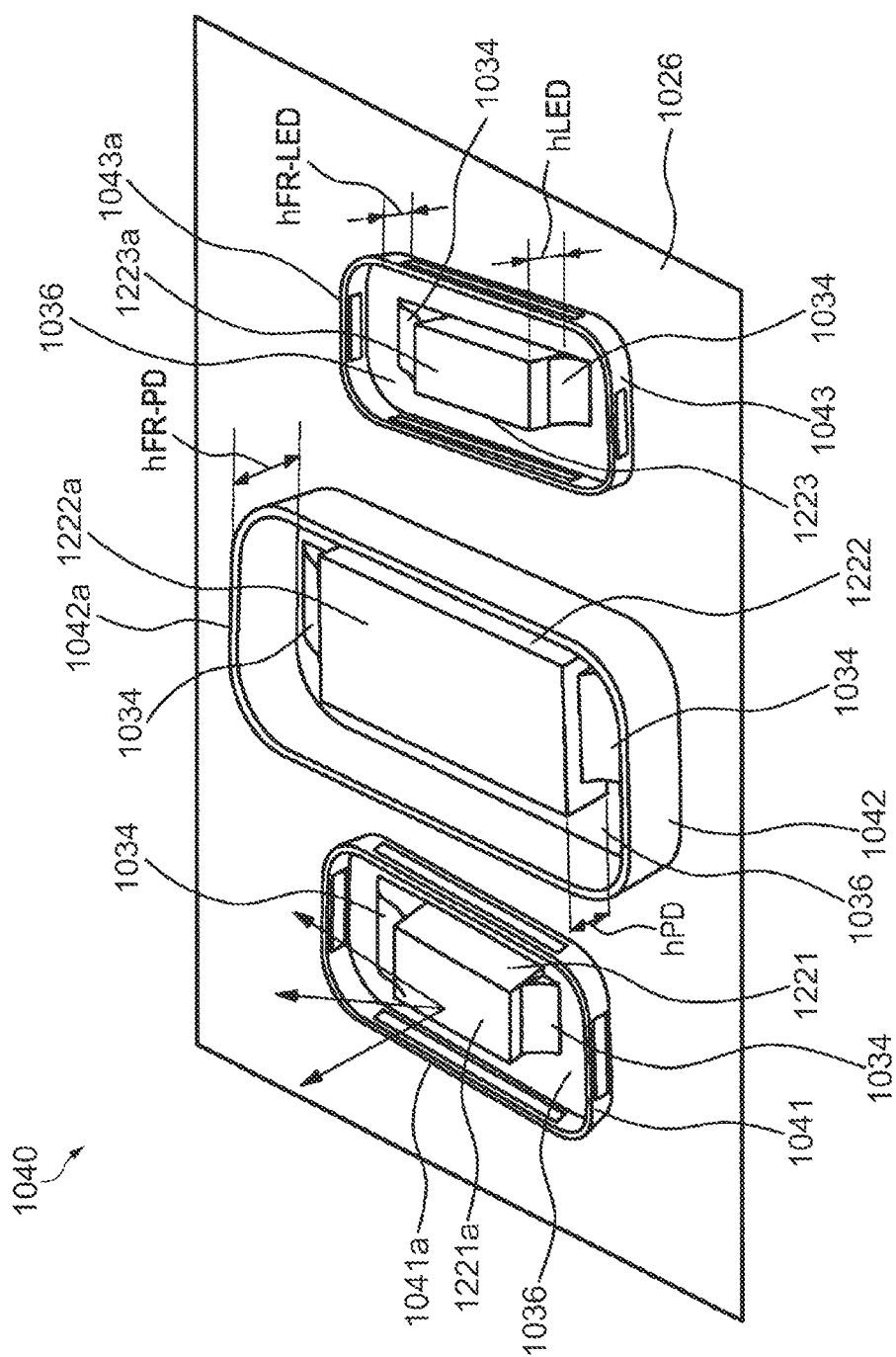
FIG. 12 is a perspective view showing a biological information measuring device according to a seventh embodiment.

The biological information measuring device 1040 according to the seventh embodiment is explained with reference to FIG. 12. FIG. 12 is a perspective view showing the biological information measuring device according to the seventh embodiment. In the biological information measuring device 1040 according to the seventh embodiment, created frames 1041, 1042, and 1043 are disposed. The frames 1041, 1042, and 1043 are disposed around the light emitting elements 1221 and 1223 and the light receiving element 1222. Gaps 1036 are formed between the frames 1041, 1042, and 1043 and the light emitting elements 1221 and 1223 and the light receiving element 1222.

An insulative material (not shown in FIG. 12) is injected using the frames 1041, 1042, and 1043 as guides to cover the electric connection terminals 1034 of the light emitting elements 1221 and 1223 and the light receiving element 1222.

In the example shown in the sixth embodiment, the light emitting elements 1221 and 1223 and the light receiving element 1222 are surrounded by the respective frames 1041, 1042, and 1043. Note that, as another example, all the frames 1041, 1042, and 1043 may be combined with one another or all the sensor elements may be surrounded by an integral frame.

As improvements for not affecting the functions of the biological information measuring device 1040, upper edges 1041a and 1043a of the frames 1041 and 1043 around the light emitting elements 1221 and 1223 are desirably lower than the upper surfaces 1221a and 1223a of the light emitting elements 1221 and 1223. In other words, a distance hFR-LED between the upper edges 1041a and 1043a of the separate frames 1041 and 1043 and the carrier 1026 is the same as or smaller than a distance hLED between the upper surfaces 1221a and 1223a of the light emitting elements 1221 and 1223 surrounded by the separate frames 1041 and 1043 and the carrier 1026 (hFR-LEDhLED).

The distance hLED between the upper surfaces 1221a and 1223a of the light emitting elements 1221 and 1223 and the carrier 1026 and the distance hFR-LED between the upper edges 1041a and 1043a of the frames 1041 and 1043 and the carrier 1026 are desirably set in a range of 0.1 mm to 0.8 mm. Note that the distance hLED between the upper surfaces 1221a and 1223a of the light emitting elements 1221 and 1223 and the carrier 1026 and the distance hFR-LED between the upper edges 1041a and 1043a of the frames 1041 and 1043 and the carrier 1026 are more desirably set in a range of 0.2 mm to 0.5 mm.

The upper edge 1042a of the frame (a receiver frame) 1042 around the light receiving element 1222 is desirably higher than the upper surface 1222a of the light receiving element 1222. In other words, a distance hFR-PD between the upper edge 1042a of the frame 1042 and the carrier 1026 is larger than a distance hPD between the upper surface 1222a of the light receiving element 1222 surrounded by the frame 1042 and the carrier 1026 (hFR-PD>hPD).

A difference between the distance hPD between the upper surface 1222a of the light receiving element 1222 and the carrier 1026 and the distance hFR-PD between the upper edge 1042a of the frame 1042 and the carrier 1026 is desirably set in a range of 0 mm to 0.5 mm. Note that the difference between the distance hPD between the upper surface 1222a of the light receiving element 1222 and the carrier 1026 and the distance hFR-PD between the upper edge 1042a of the frame 1042 and the carrier 1026 is more desirably set in a range of 0.1 mm to 0.2 mm.

Further, the distance hFR-PD between the upper edge 1042a of the frame 1042 and the carrier 1026 is larger than the distance hLED between the upper surfaces 1221a and 1223a of the light emitting elements 1221 and 1223 and the carrier 1026 (hFR-PD>hLED).

Note that, for example, when the light receiving element 1222 and the light emitting elements 1221 and 1223 are close to each other, only one frame wall may be present between the light receiving element 1222 and the light emitting elements 1221 and 1223. This sometimes occurs because of manufacturing easiness. When the one frame wall is a case, frame walls of both the frames coincide with each other in the light receiving element 1222 and the light emitting elements 1221 and 1223. This means that the frame walls of the light emitting elements 1221 and 1223 are higher. Specifically, in the frames 1041 and 1043 surrounding the light emitting elements 1221 and 1223, the frame wall on a side where the light receiving element 1222 is present is high. The other frame walls are lower than the upper surfaces 1221a and 1223a of the light emitting elements 1221 and 1223.

Further, instead of the frames 1041, 1042, and 1043, a first wall section may be provided between the light receiving element 1222 and the light emitting element 1221 or 1223. A second wall section may be provided on the outer side of the light emitting elements 1221 and 1223, that is, on the opposite side of the first wall section with respect to the light receiving element 1222.

With such a configuration, the distance between the carrier 1026 and the upper surface of the first wall section may be larger than the distance between the carrier 1026 and the upper surface of the second wall section. With such a configuration, it is possible to realize the functions of the frames with a smaller number of members compared with when the frames are configured to surround the light emitting elements and the light receiving element as shown in FIG. 12.

Note that, by using the frames 1041 and 1043 and the frame 1042 as in the seventh embodiment, it is possible to prevent the injected insulative material such as epoxy resin from flowing out. Creating an additional structure to divide the insulative material such as epoxy resin in this way is an option for enabling high mass productivity. Note that the frames 1041 and 1043 and the frame 1042 may be made of a material same as the material of the carrier 1026. For example, the frames may be formed by injection molding using, for example, epoxy resin or polycarbonate resin.

As explained above, the insulative material 1032 (see FIG. 10) protects the electric connection terminals 1034 of the sensor elements (the light emitting elements 1221 and 1223 and the light receiving element 1222). However, the electric connection terminals 1034 have to be further set in contact with other elements, that is, additional electronic devices (e.g., a driver, detection electronics, a processor, or a power supply). This means that the carrier 1026 (or a printed board (PCB)) has some electric connection to the additional electronic devices.

Eighth Embodiment

Figure 13:
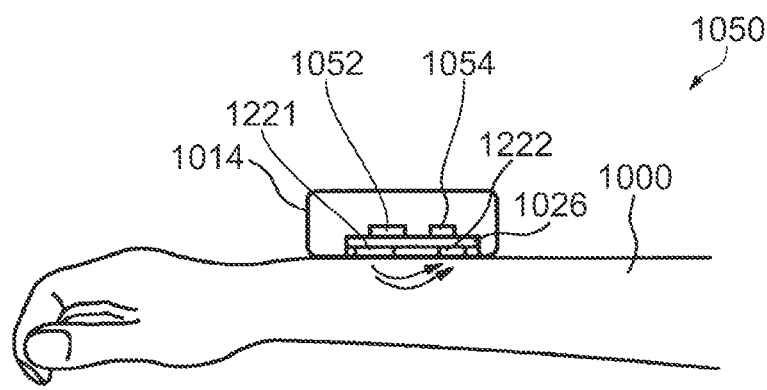
FIG. 13 is a sectional view showing a biological information measuring device according to an eighth embodiment.

A biological information measuring device according to an eighth embodiment is explained with reference to FIG. 13. FIG. 13 is a sectional view showing the biological information measuring device according to the eighth embodiment. A biological information measuring device 1050 according to the eighth embodiment includes the additional electronic devices (e.g., a processor 1052 and a driver 1054). External electric connection terminals (not shown in the figure) are not disposed on the carrier 1026 on which the sensor elements (the light emitting element 1221 and the light receiving element 1222) are disposed. That is, the additional electronic devices are disposed on a carrier or aboard separate from the sensor elements. With such a configuration, it is possible to mount necessary additional electronic devices on the biological information measuring device 1050 while maintaining satisfactory contact of the skin and the sensor elements (the light emitting element 1221 and the light receiving element 1222). For example, the external electric connection terminals can be disposed on a side surface of the carrier 1026.

As explained above, the different kinds of sensors can be used in the biological information measuring device according to the invention. For example, when the light receiving element 1222 is an electric sensor, two skin conductance electrodes (e.g., the sensor elements (the light emitting element 1221 and the light receiving element 1222 shown in FIG. 10)) for measuring the conductivity of the user are covered with the skin. Note that further two or more kinds of sensors can be used in the biological information measuring device of this type. Further, the number of sensor elements may be any number.

In the fifth to eighth embodiments, a proposed method of manufacturing the biological information measuring device that measures the physiological parameters is explained.

First, in a first step, the sensor 1022 including at least the two sensor elements (the light emitting element 1221 and the light receiving element 1222) for detecting a sensor signal is disposed on the carrier 1026. Subsequently, in a second step, electric contacts of the sensor elements are formed on the carrier 1026. Subsequently, in a third step, the one or more frames 1041 and 1042 are formed on the carrier 1026 around the sensor 1022 and/or the respective sensor elements (the light emitting element 1221 and the light receiving element 1222). In a fourth step, the insulative material 1032 is injected and filled in regions surrounded by the respective frames 1041 and 1042 that do not cover the upper surfaces 1221a and 1222a of the sensor elements (the light emitting element 1221 and the light receiving element 1222) included in the carrier 1026.

According to the fifth to eighth embodiments, a method for achieving protection of electric contacts not adversely affecting the performance of the biological information measuring device is proposed. The frames 1041 and 1043 are formed by a method of keeping the performance of the sensors. For example, at least one of the frames 1041 and 1043 prevents the positions of the sensors on the entire skin from shifting. Further, at least one of the frames 1041 and 1043 can be useful for preventing emitted direct light from being input to the light receiving element 1222. The height of the frames 1041 and 1043 around the light emitting elements 1221 and 1223 on a side to which the light receiving element 1222 is directed desirably has to be smaller than the height of the upper surfaces 1221*a* and 1223*a* of the light emitting elements 1221 and 1223. In addition, the frame 1042 around the light receiving element 1222 may be higher than the upper surface 1222*a* of the light receiving element 1222.

Ninth Embodiment

The biological information measuring devices in the first to eighth embodiments may include various sensors such as a strain gauge, a thermometer, a clinical thermometer, an acceleration sensor, a gyro sensor, a piezoelectric sensor, an atmospheric pressure sensor, a manometer, an electrochemical sensor, a GPS (Global Positioning System), and a vibrometer. Since the biological information measuring devices include these sensors, it is possible to derive information concerning a physiological state of an individual on the basis of data indicating one or one or more physiological parameters such as a heartbeat, a pulse, a variation between pulsations, an EKG (ElectroKardiogram), an ECG (Electrocardiogram), a breathing rate, a skin temperature, a body temperature, a heat flow of a body, an electric skin reaction, a GSR (Galvanic skin reflex), an EMG (Electromyogram), an EEG (electroencephalogram), an EOG (Electrooculography), a blood pressure, a body fat, a hydration level, an activity level, a body motion, an oxygen consumption, glucose, a blood sugar level, a muscle mass, pressure on muscles, pressure on bones, ultraviolet ray absorption, a sleeping state, a physical condition, a stress state, and a posture (e.g., lying, upright, or sitting). Values obtained by the various sensors may be transmitted to a portable communication terminal such as a smart phone, a cellular phone, or a future phone or an information processing terminal such as a computer or a tablet computer to execute arithmetic processing of the physiological parameters in the portable communication terminal or the information processing terminal.

Before measuring biological information, the user inputs a profile of the user to the biological information measuring device, the portable communication terminal, or the information processing terminal. Consequently, in order to maximize the possibility of establishing and maintaining a recommended healthy life style on the basis of the profile and a biological information measurement result, the user can receive provision of characteristic information peculiar to the user and environment information that need to be treated. Examples of the presented information include one kind or a plurality of kinds of information including exercise information such as an exercise type, exercise intensity, and an exercise time, meal information such as a meal time, an amount of meals, recommended intake food materials and intake menus, and intake food materials and intake menus that should be avoided, life support information such as a sleep time, depth of sleep, quality of sleep, a wakeup time, a bed time, a working time, stress information, a consumed calorie, an intake calorie, and a calorie balance, body information such as basal metabolism, a body fat amount, a body fat percentage, and a muscle mass, medication information, supplement intake information, and medical information.

Examples of the profile of the user input beforehand include one or a plurality of, for example, an age, a date of birth, sex, a hobby, an occupation category, a blood type, a sports history in the past, an activity level, meals, regularity of sleep, regularity of a bowel habit, situation adaptability, persistence, responsiveness, strength of reaction, a personality of the user such as characters, an independency level of the user, self-organization, self-management, sociability, a memory and an academic accomplishment ability, an awakening level of the user, attentiveness of the user including cognition speed, an avoidance ability for an attentiveness hindrance factor, and an awakening state and a self-control ability, an attention maintenance ability, weight, height, a blood pressure, a health state of the user, a diagnosis result by a doctor, a diagnosis date by the doctor, presence or absence of contact with the doctor and a health manager, drugs and supplements currently taken, presence or absence of allergies, an allergy history, a present allergy symptom, an opinion concerning a behavior related to health, a disease history of the user, a surgery history of the user, a family history, a social event such as a divorce or unemployment that required adjustment by an individual, an opinion concerning health priority of the user, a sense of value, an ability to change a behavior, an event considered to be a stress cause of life, a stress management method, a self-consciousness degree of the user, an empathy degree of the user, an authority transfer degree of the user, self-respect of the user, exercise of the user, a sleep state, a relaxed state, a present routine of everyday activities, a personality of an important person (e.g., a spouse, a friend, a colleague, or a superior) in the life of the user, and a perception of the user concerning whether a collision inhibiting a healthy life style or contributing to stress in a relation with the important person is present.

Figure 14:
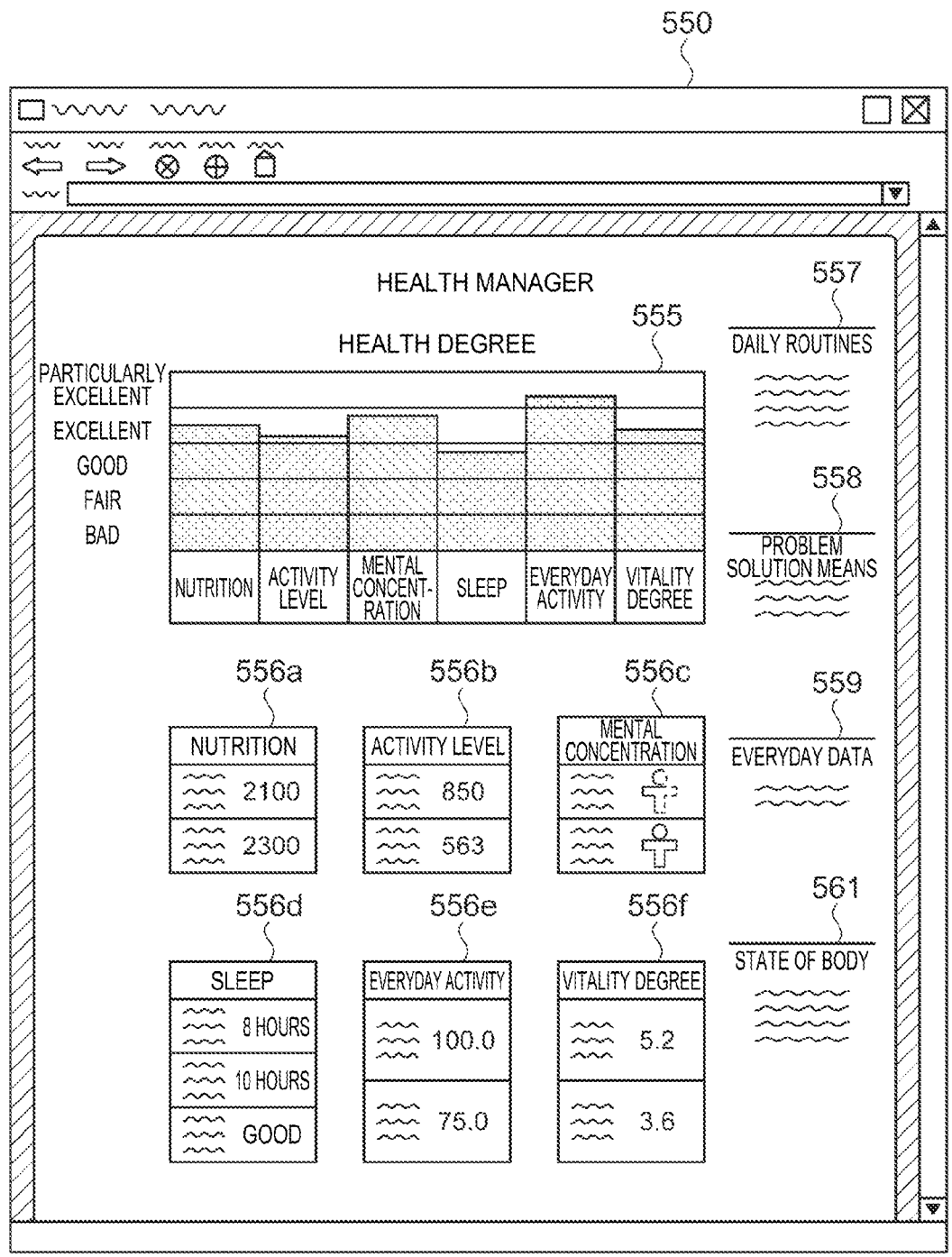
FIG. 14 is a diagram showing an overview of a Web page serving as a start point of a health manager in a biological information measuring device according to a ninth embodiment.
Figure 15:
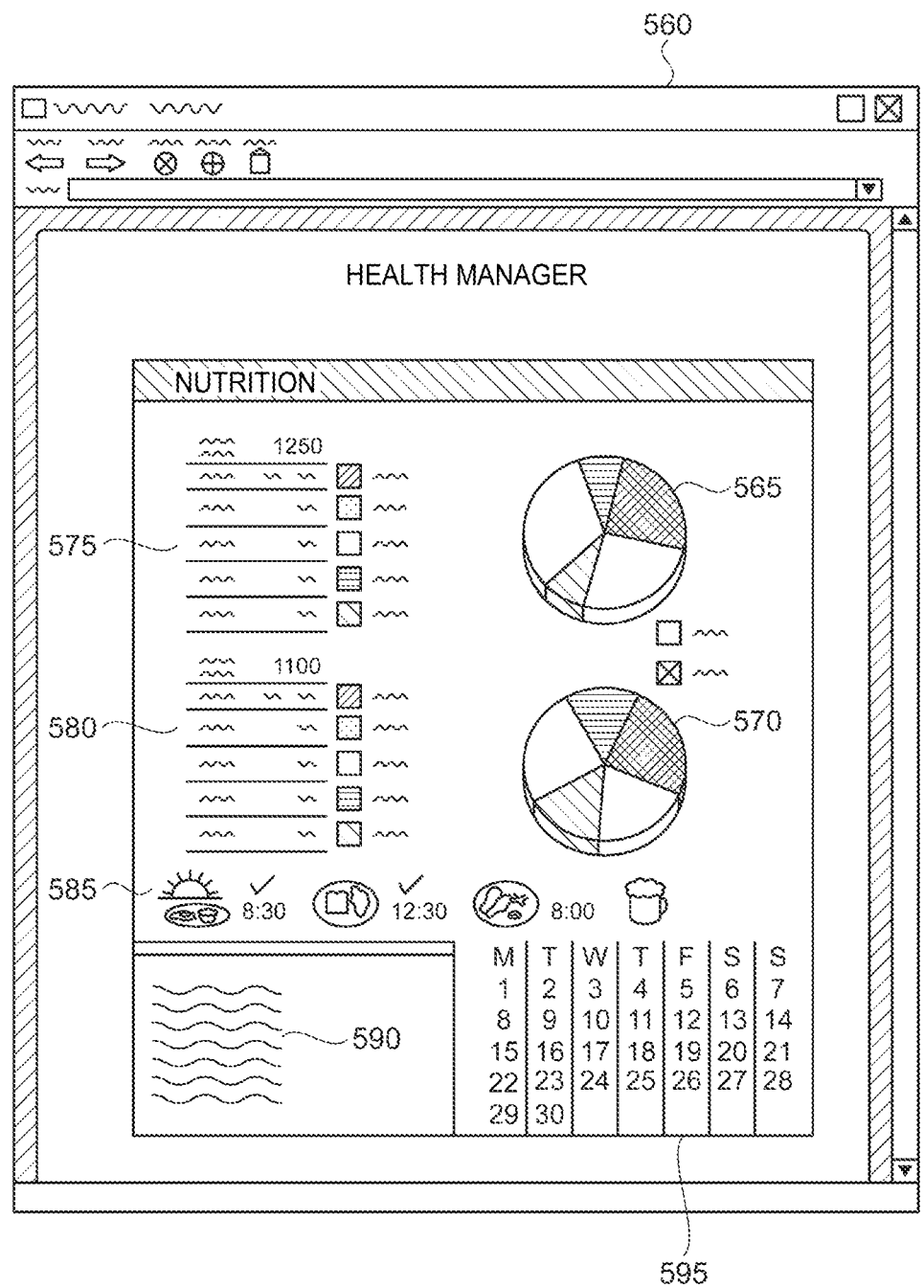
FIG. 15 is a diagram showing an example of a nutrition Web page.
Figure 16:
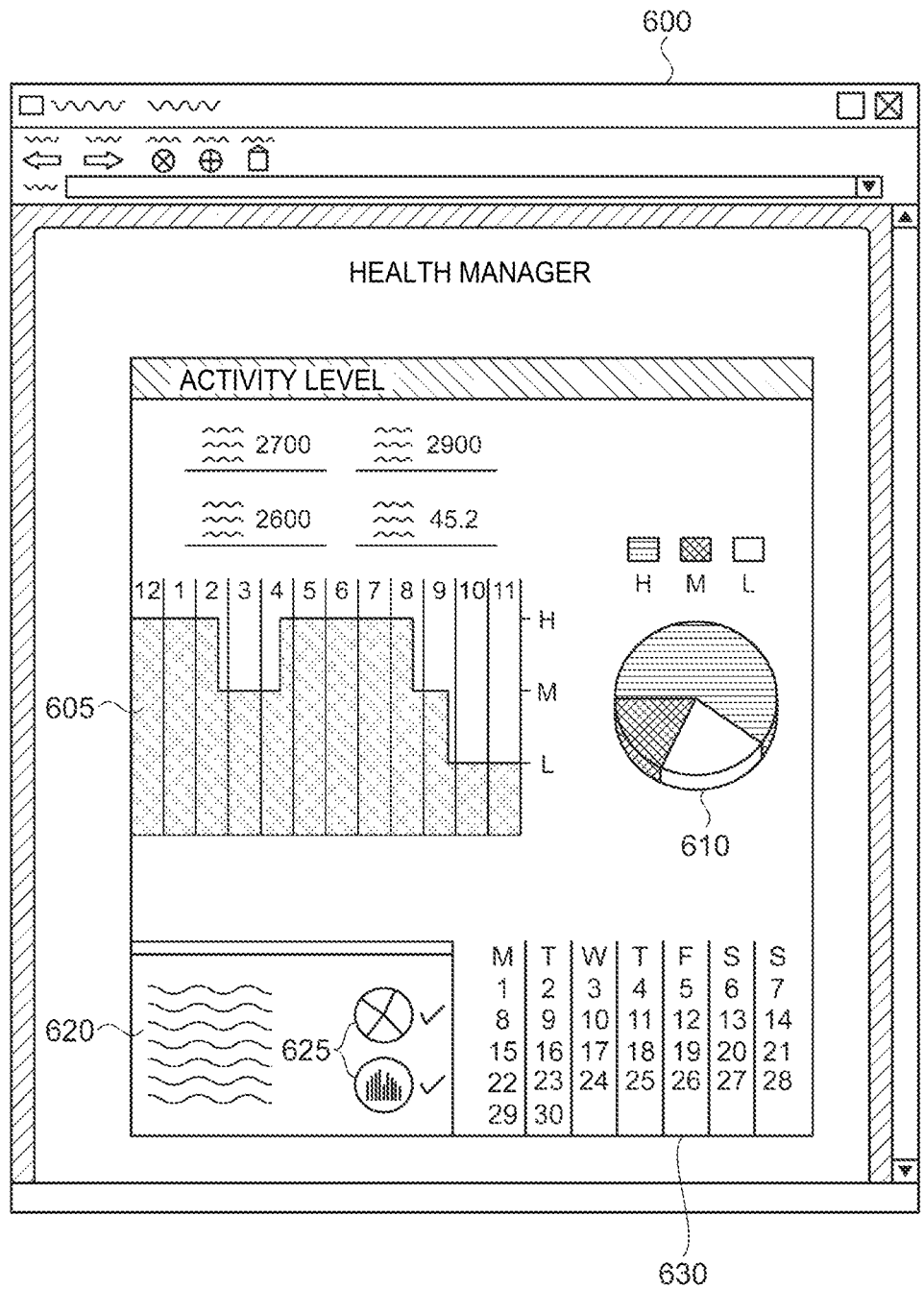
FIG. 16 is a diagram showing an example of an activity level Web page.
Figure 17:
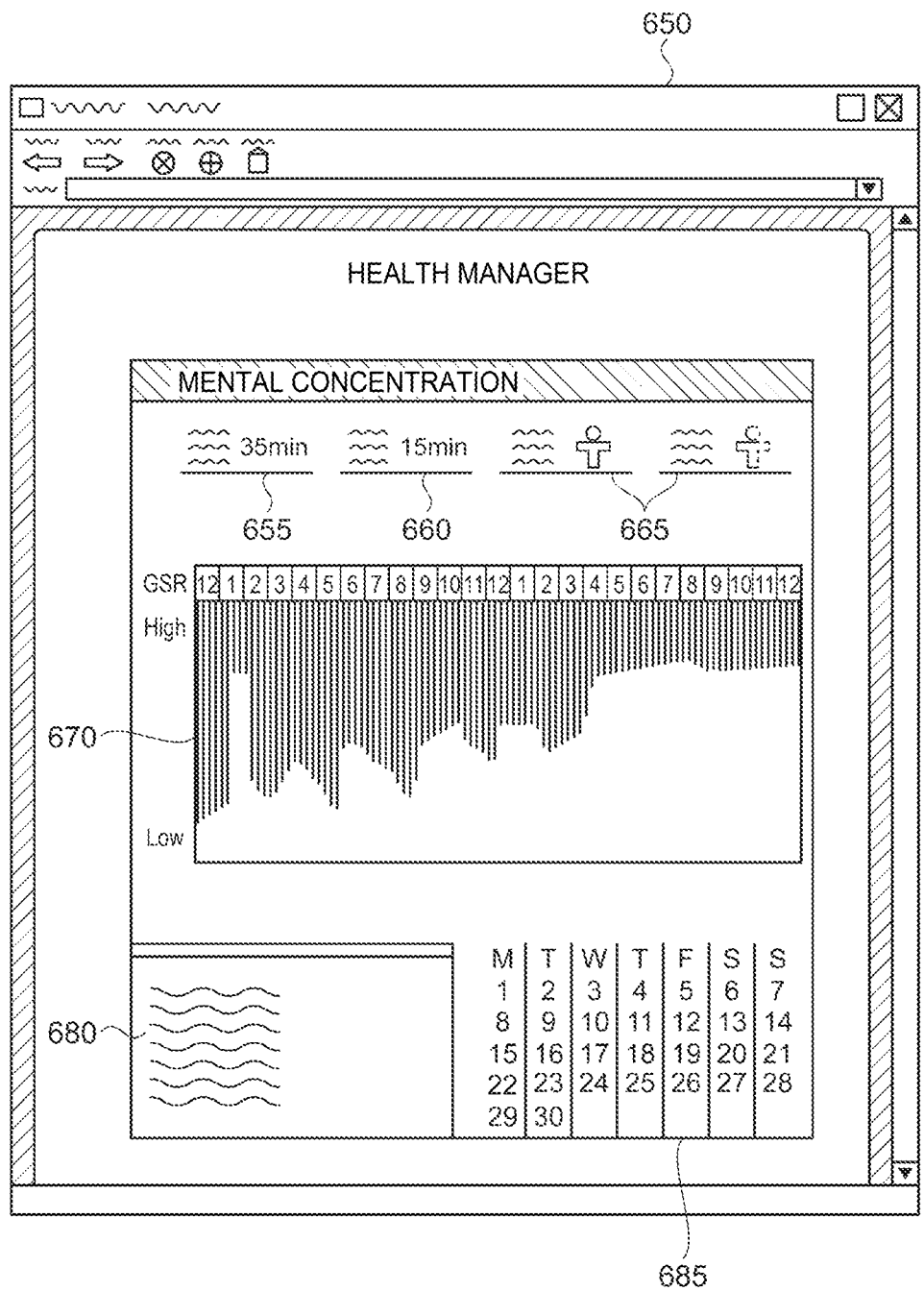
FIG. 17 is a diagram showing an example of a mental concentration Web page.
Figure 18:
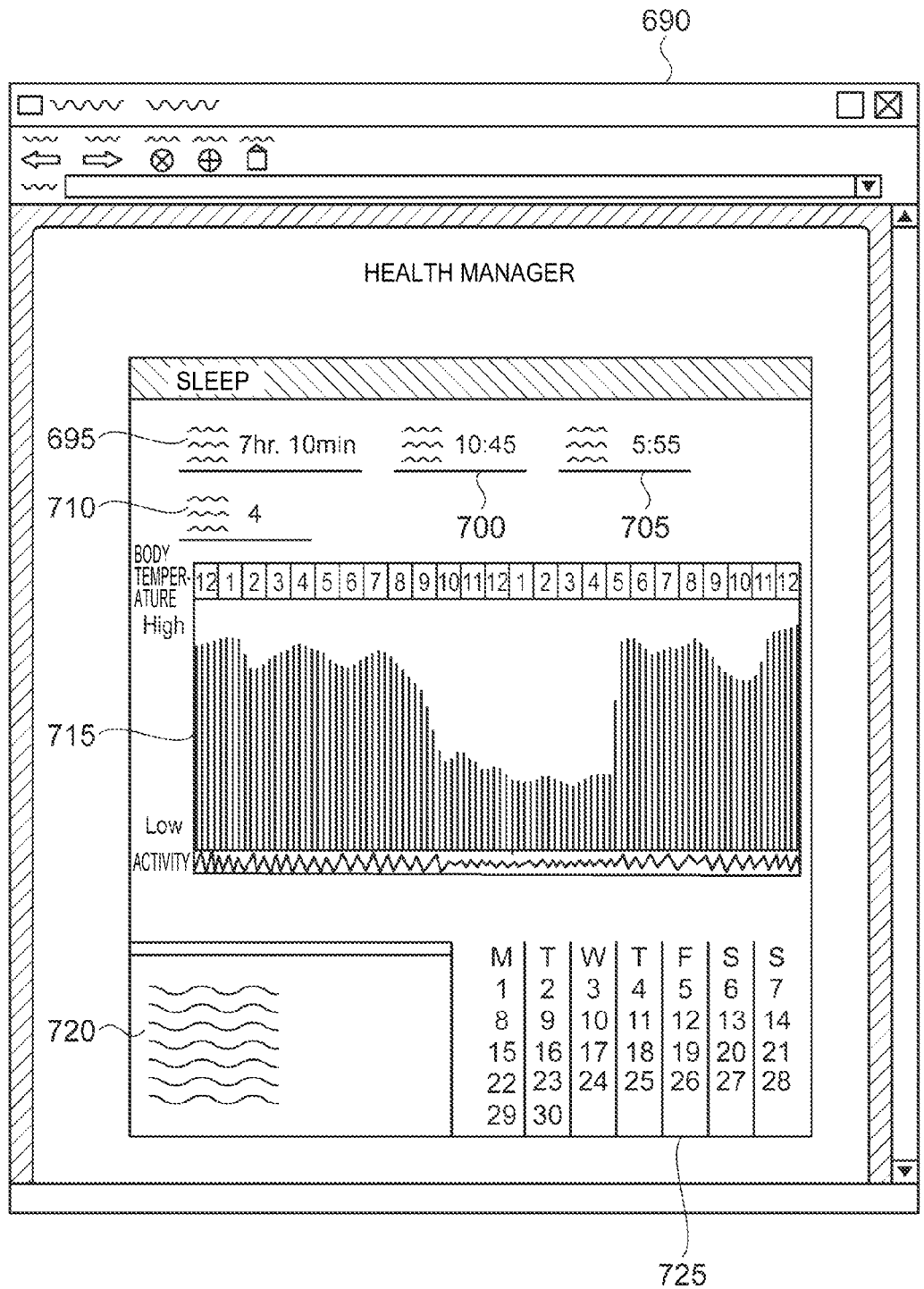
FIG. 18 is a diagram showing an example of a sleep Web page.
Figure 19:
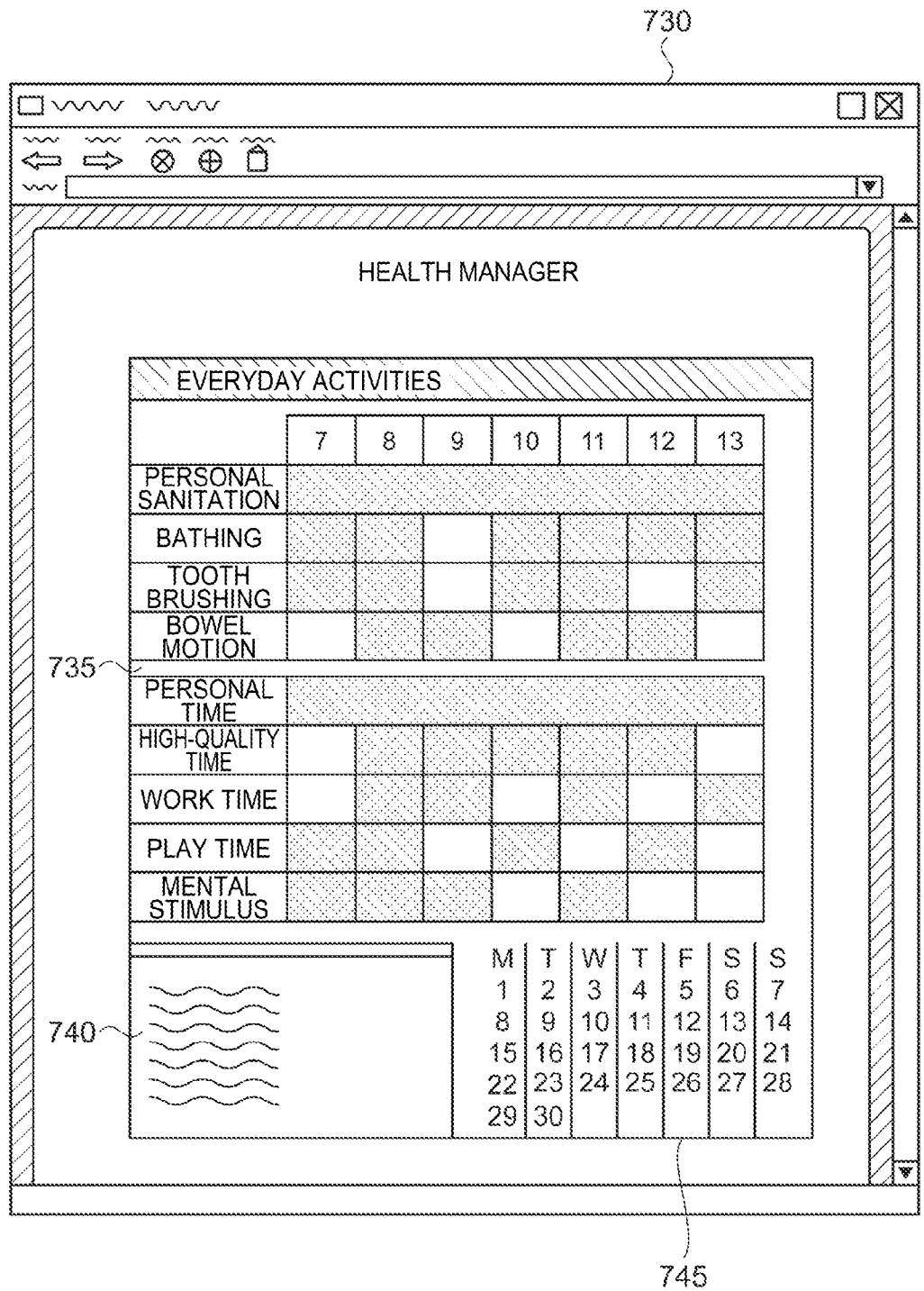
FIG. 19 is a diagram showing an example of an everyday activity Web page.
Figure 20:
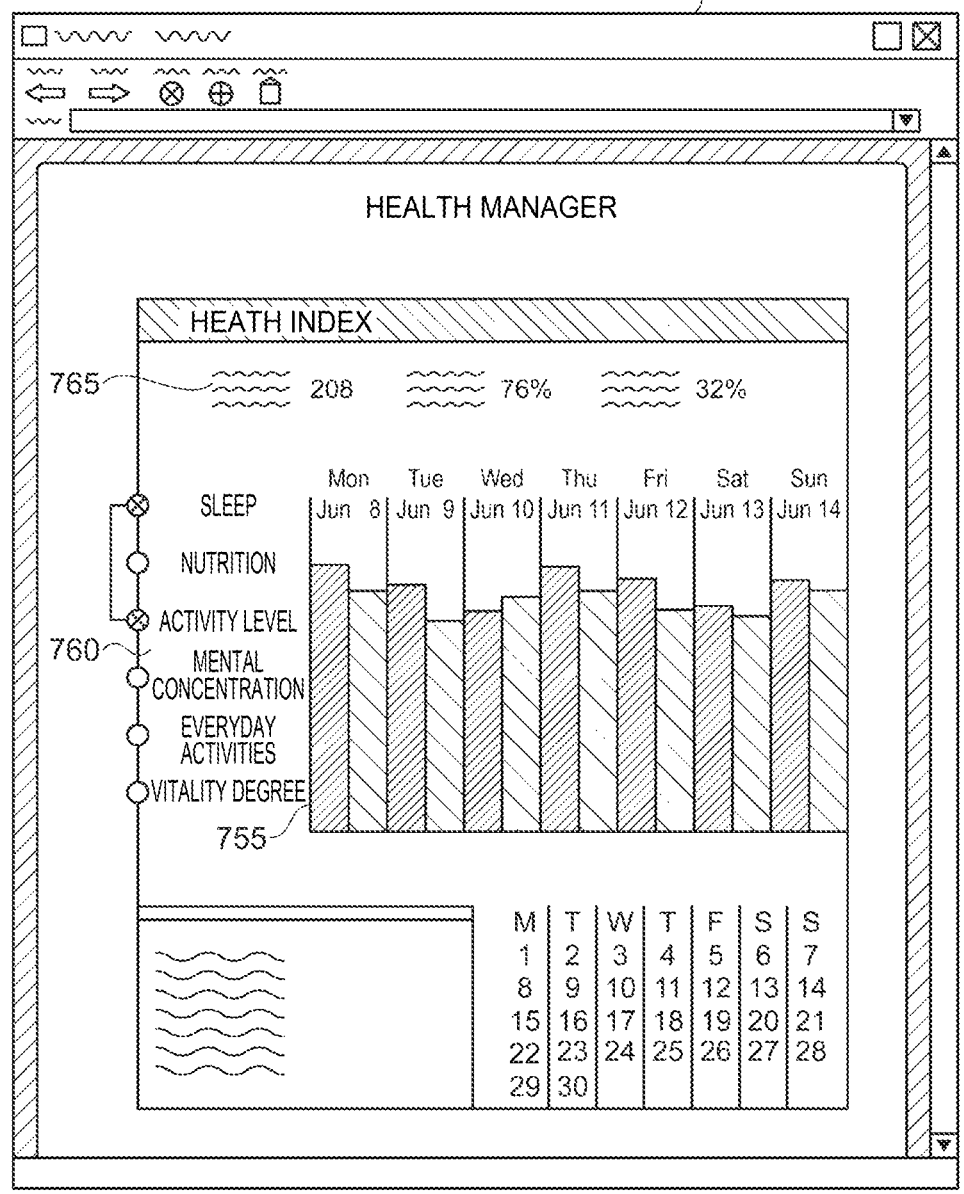
FIG. 20 is a diagram showing an example of a health degree Web page.

A biological information measuring device according to a ninth embodiment that can receive provision of characteristic information peculiar to the user and environment information, which need to be treated, in order to maximize the possibility of establishing and maintaining a recommended healthy life style is explained with reference to FIGS. 14 to 20. FIG. 14 is a diagram showing an overview of a Web page serving as a start point of a health manager in the biological information measuring device according to the ninth embodiment. FIG. 15 is a diagram showing an example of a nutrition Web page. FIG. 16 is a diagram showing an example of an activity level Web page. FIG. 17 is a diagram showing an example of a mental concentration Web page. FIG. 18 is a diagram showing an example of a sleep Web page. FIG. 19 is a diagram showing an example of an everyday activity Web page. FIG. 20 is a diagram showing an example of a health degree Web page.

Although not shown in the figure, the biological information measuring device according to the ninth embodiment includes, for example, a sensor device connected to a microprocessor. In the biological information measuring device according to the ninth embodiment, data concerning various life activities finally sent to a monitor unit and stored and personal data or life information input by the user from a Web site maintained by the monitor unit are processed by the microprocessor and provided as biological information. A specific example is explained below.

The user accesses a health manager for the user via a Web page, application software, or other communication media. In FIG. 14, a Web page 550 serving as a start point of the health manager is shown as an example. In the Web page 550 of the health manager shown in FIG. 14, various data are provided to the user. The data provided in this way are one or more of, for example, (1) data indicating various physiological parameters based on values measured by various sensor devices, (2) data derived from the data indicating the various physiological parameters, and (3) data indicating various context parameters generated by the sensor devices and data input by the user.

Analysis state data has a characteristic in using a certain specific utility or algorithm in order to convert one or more of (1) data indicating various physiological parameters acquired by the sensor devices, (2) data derived from the various physiological parameters, and (3) data indicating various context parameters acquired by the sensor devices and data input by the user into a health degree, a robustness degree, a life style index, or the like obtained by calculation. For example, a calorie, amounts of protein, fat, carbohydrate, and a certain specific vitamin, and the like can be calculated on the basis of data input by the user in relation to intake foods. As another example, an index of a stress level for a desired time can be provided to the user by using a skin temperature, a heart rate, a breathing rate, a heat flow, and/or a GSR. As still another example, an index of a sleep pattern for a desired time can be provided to the user by using a skin temperature, a heat flow, a variation between pulsations, a heart rate, a pulse, a breathing rate, a center part body temperature, an electric skin reaction, an EMG, an EEG, an EOG, a blood pressure, an oxygen consumption, ambient sound, and a motion of the body detected by a device such as an accelerometer.

On the Web page 550 shown in FIG. 14, a health index 555 serving as a health degree is displayed. The health index 555 is a graphic utility for measuring an achievement of a user and a degree of attainment of healthy daily routines for feeding back the achievement and the degree to member users. In this way, the health index 555 shows, to the member users, health states of the member users and progress states of behaviors concerning health maintenance. The health index 555 includes six categories concerning health and a life style of the user, that is, nutrition, an activity level, mental concentration, sleep, everyday activities, and a vitality degree (a general impression). The category of "nutrition" relates to information concerning what, when, and how much the person (the user) ate and drank. The category of "activity level" relates to an exercise amount indicating how much the person moves around. The category of "mental concentration" relates to the quality (ability) of an activity for changing to the person to a relaxed state in a highly concentrated state of the person (the user) and time in which the person concentrates in the activity. The category of "sleep" relates to the quality and the quantity of sleep of the person (the user). The category of "everyday activities" relates to activities the person (the user) has to do every day and health risks that the person encounters. The category of "vitality degree (impression)" relates to a generation perception concerning whether vitality is high in a certain specific day. The categories desirably include level indicators or bar graphs indicating, using scales changing between "bad" and "particularly excellent", what kinds of achievements the user made concerning the categories.

When the member users end a first investigation explained above, a profile for providing the user with a summary of characteristics of the user and a life environment is created and recommended healthy daily routines and/or targets are presented. The recommended healthy daily routines include any combination of specific advices concerning appropriate nutrition, exercise, mental concentration, and every day activities (life) of the user. An exemplary schedule or the like may be presented as a guide indicating how activities related to the recommended healthy daily routines are adopted in the life of the user. The user periodically takes the investigation and practices the above-mentioned items on the basis of a result of the investigation.

The category of "nutrition" is calculated from both of data input by the user and data sensed by the sensor device. The data input by the user includes hours and drinking and eating times of breakfast, lunch, dinner, and optional snacks, foods to be drunk and eaten, supplements such as vitamins, and water and other liquid (drinking water and liquid foods) to be drunk during time selected in advance. The central monitor unit calculates, on the basis of the data and accumulated data concerning publicly-known characteristics of various foods, well-known nutritional values such as a consumed calorie and contents of protein, fat, carbohydrate, and vitamin.

In the category of "nutrition", recommended healthy daily routines can be determined on the basis of the bar graph indicating nutrition of the health index 555. The recommended healthy daily routines can be adjusted on the basis of information such as sex, age, and height and weight of the user. Note that the user can set or a substitute of the user can set, on behalf of the user, a calorie to be taken every day, amounts of nutrients such as protein, fiber, fat, and carbohydrate and water, and a target of a certain specific nutrient concerning a ratio to an overall intake amount. Parameters used for the calculation of the bar graphs include the number of times of meals in one day, a consumption of water, and types and amounts of foods eaten every day input by the user.

The nutritional information is presented to the user by a nutrition Web page 560 shown in FIG. 15. The nutrition Web page 560 desirably includes nutrition numerical value charts 565 and 570 respectively indicating actual and target numerical values of nutrition as pie graphs and nutrition intake charts 575 and 580 respectively indicating an actual nutrition intake total amount and a target nutrition intake total amount. The nutrition numerical value charts 565 and 570 desirably indicate items such as carbohydrate, protein, and fat as percentages. The nutrition intake charts 575 and 580 desirably indicate total values and target values of calories separately for components such as fat, carbohydrate, protein, and vitamin. The nutrition Web page 560 also includes a history 585 indicating times in which foods and water were consumed, a hyperlink 590 for enabling the user to directly check news articles related to nutrition, advices for improving daily routines concerning nutrition, and related advertisements somewhere on a network, and a calendar 595 for enabling the user to select an applicable period and the like. Items indicated by the hyperlink 590 can be selected on the basis of information that could have been known concerning an individual through an investigation and an achievement of the individual measured by the health index.

The category of "activity level" of the health index 555 is designed to support a check by the user concerning when and how the user acted (moved) in the day. Both of data input by the user and data sensed by the sensor device are used. The data input by the user includes a detailed item concerning everyday activities of the user indicating that, for example, the user works at a desk from 8:00 am to 5:00 pm and thereafter takes an aerobics lesson from 6:00 pm to 7:00 pm. The related data sensed by the sensor device includes a heart rate, exercise sensed by a device such as an accelerometer, a heat flow, a breathing rate, a consumed calorie amount, a GSR, and a hydration level. These data can be extracted by the sensor device or the central monitor unit. The consumed calorie amount can be calculated by various methods such as a multiplication of a type of exercise input by the user and duration of the exercise input by the user, a multiplication of sensed exercise and time of the exercise and a filter constant, and a multiplication of a sensed heat flow, time, and a filter constant.

In the category of "activity level", recommended healthy daily routines can be determined on the basis of the bar graph indicating the activity level of the health index 555. The recommended healthy routines are, for example, a minimum target calorie consumed in an activity. Note that the minimum target calorie can be set on the basis of information such as sex, age, height, and weight of the user. Parameters used for the calculation of the bar graph include times consumed for various kinds of exercise and energetic life style activities and input by the user and/or sensed by the sensor device and a calorie burned more than an energy consumption parameter calculated in advance.

Information concerning an activity (a movement) of an individual user is presented to the user by an activity level Web page 600 shown in FIG. 16. The activity level Web page 600 includes an activity degree graph 605 in a form of bar graphs for monitoring activities of the user in three categories, that is, "high", "medium", and "low" concerning a predetermined unit time. An activity percentage chart 610 in a form of a pie graph can be presented to indicate percentages in a predetermined period such as one day of consumptions in the respective categories by the user. In the activity level Web page 600, calorie indicators (not shown in the figure) for displaying items such as a burned calorie total amount, an everyday burned calorie target value, a calorie intake total value, and an aerobics exercise time can also be provided. The activity level Web page 600 includes at least one hyperlink 620 for enabling the user to directly check related news articles, advices for improving daily routines concerning an activity level, and related advertisements somewhere on a network.

The activity level Web page 600 can be viewed in various formats. The activity level Web page 600 can enable the user to select a bar graph, a pie graph, or both of the graphs or a chart. The user can select the graph or the chart in an activity level checkbox 625. An activity level calendar 630 is presented to enable the user to select an applicable period and the like. Items shown in the hyperlink 620 can be selected on the basis of information extracted from the individual by an investigation and an achievement measured by the health index.

The category of "mental concentration" of the health index 555 is designed to support the user in monitoring a parameter concerning time in which the user performs an activity for enabling the body to reach a deep relaxed state while concentrating. The category of "mental concentration" is based on both of data input by the user and data sensed by the sensor device. Specifically, the user can input a start time and an end time of a relaxing activity such as yoga or meditation. The quality of these activities determined by the depth of the mental concentration can be measured by monitoring parameters including a skin temperature, a heart rate, a breathing rate, and a heat flow sensed by the sensor device. A percentage change of a GSR obtained by the sensor device or the central monitor unit can also be used.

In the category of "mental concentration", recommended healthy daily routines can be determined on the basis of a bar graph indicating an activity level of mental concentration of the health index 555. Everyday participation in an activity for deeply relaxing the body while keeping a highly concentrated state is included in the recommended healthy daily routines and displayed. Parameters used for calculation of the bar graph include the length of time consumed for a mental concentration activity, the depth of the mental concentration activity, or a percentage change of a skin temperature, a heart rate, a breathing rate, a heat flow, or a GSR sensed by the sensor device from a baseline indicating quality.

Information concerning time consumed for a behavior for deeply thinking back on the user himself or herself (reflection) and a mental concentration activity for, for example, deeply relaxing the body is presented to the user by a mental concentration Web page 650 shown in FIG. 17. Note that the mental concentration activity is sometimes called session. The mental concentration Web page 650 includes time 655 consumed for the session, a target time 660, a comparison portion 665 indicating a target value and an actual value of the depth of mental concentration, and a histogram 670 indicating an overall stress level derived from, for example, a skin temperature, a heart rate, a breathing rate, a heat flow, and/or a GSR.

In the comparison portion 665, a contour of a human indicating a target mental concentration state is indicated by a solid line. A contour of the human indicating an actual mental concentration state changes between a blurred state (in FIG. 17, indicated by a broken line) and the solid line according to a level of mental concentration. The mental concentration Web page 650 desirably includes a hyperlink 680 for enabling the user to directly check related news articles, advices for improving daily routines concerning mental concentration, and related advertisements somewhere on a network and a calendar 685 for enabling the user to select an applicable period. Items indicated by the hyperlink 680 can be selected on the basis of information that could have been known from an individual through an investigation and an achievement of the individual measured by the health index.

The category of "sleep" of the health index 555 is designed to be capable of supporting the user in monitoring a sleep pattern and the quality of sleep. The category is intended to help the user to learn about the importance of sleep in a healthy life style and a relation of sleep with a daily cycle, which is a normal everyday change of functions of the body. The category of "sleep" is based on both of data input by the user and data sensed by the sensor device. Data input by the user during related time intervals includes bedtime and wakeup time (a sleep time) of the user and a rank of the quality of sleep. Related data obtained from the sensor device includes a skin temperature (a body temperature), a heat flow, a variation between pulsations, a heart rate, a pulse rate, a breathing rate, a center part body temperature, an electric skin reaction, an EMG, an EEG, and EOG, a blood pressure, and an oxygen consumption. Ambient sound and a movement of the body detected by a device such as an accelerometer also have a relation. Thereafter, bedtime and wakeup time, sleep suspension and the quality of sleep, the depth of sleep, and the like can be calculated and derived using the data.

The bar graph indicating sleep of the health index 555 is displayed concerning healthy daily routines including securing of a desirable minimum sleep time of every night, predictable bedtime, and predictable wakeup time. Specific parameters for enabling calculation of the bar graph include bedtime and wakeup time of every day sensed by the sensor device or input by the user and the quality of sleep graded by the user or derived from other data.

The information concerning sleep is presented to the user by a sleep Web page 690 shown in FIG. 18. The sleep Web page 690 includes asleep time indicator 695 based on data from the sensor device or data input by the user, a user bedtime indicator 700, and a user wakeup time indicator 705. Note that the quality of sleep input by the user can also be displayed using a sleep quality rank 710. When display exceeding a time interval of one day is performed on the sleep Web page 690, the sleep time indicator 695 can be displayed as a cumulative value and the bedtime indicator 700, the wakeup time indicator 705, and the sleep quality rank 710 can be calculated as average values and displayed. The sleep Web page 690 also includes a sleep graph 715, which is selectable by the user, for calculating and displaying one sleep related parameter over a predetermined time interval. FIG. 18 shows a change in a heat flow (a body temperature) in one day. The heat flow tends to be low during sleep and high when the user is awake. It is possible to obtain a biorhythm of the person from this information.

The sleep graph 715 displays, as a graph, data from an accelerometer built in the sensor device that monitors a movement of the body. The sleep Web page 690 can include a hyperlink 720 for enabling the user to directly check news articles related to sleep, advices for improving daily routines concerning sleep, and related advertisements on a network and a sleep calendar 725 for selecting a related time interval. Items indicated by the hyperlink 720 can be specially selected on the basis of information that could have been known from an individual through an investigation and an achievement of the individual measured by the health index.

The category of "everyday activities" of the health index 555 is designed to be capable of supporting the user in monitoring a specific activity related to health and safety and a risk and is solely based on data input by the user. Examples of the category of "everyday activities" concerning activities in everyday life include four categories of subordinate concepts. Specifically, the category of "everyday activities" is divided into (1) an item related to personal sanitation for enabling the user to monitor activities for, for example, caring for teeth using a toothbrush or a dental floss and taking a shower, (2) an item related to health maintenance for tracking whether the user drinks a drug or a supplement as prescribed and enabling the user to monitor, for example, consumptions of cigarettes or alcohol, (3) an item related to a personal time for enabling the user to monitor time spent together with a family or friends, leisure, and a mental concentration activity, and (4) an item related to a responsibility for enabling the user to monitor work such as household chores and livelihood activities.

In the category of "everyday activities", the bar graph indicating "everyday activities" of the health index 555 desirably indicates recommended healthy daily routines explained below. As an example of the daily routine concerning the personal sanitation, the user desirably takes a shower or a bath every day, keeps teeth clean using a brush and floss every day, and maintains a regular bowel motion. As an example of the daily routine concerning the health maintenance, the user desirably drinks a drug, a vitamin tablet, and/or a supplement, smokes, drinks, and monitors health every day with a health manager. As an example of the daily routine concerning the personal time, the user desirably creates time that user spends together with the family at least for a predetermined time every day and/or spends good time together with friends, reduces time for work, adopts time for leisure or play, and performs intellectual work. As an example of the daily routine concerning the responsibility, the user desirably performs household chores, is not late for work, and keeps a promise. The bar graph is determined according to information input by the user and/or calculated on the basis of a degree of the user completing of listed activities every day.

Information concerning these activities is presented to the user by an everyday activity Web page 730 shown in FIG. 19. An activity chart 735 in the everyday activity Web page 730 indicates whether the user executed the activities required by the daily routines. The activity chart 735 can be selected concerning one or more of subordinate concepts. In the activity chart 735, colored or shaded boxes indicate that the user executed the required activities and uncolored or unshaded boxes indicate that the user did not execute the activities. The activity chart 735 can be created and viewed in a selectable time interval. FIG. 19 shows, as an example, the categories of the personal sanitation and the personal time in a specific week. Further, the everyday activity Web page 730 can include a hyperlink 740 for enabling the user to directly check related news articles, advices for improving daily routines concerning activities of everyday life, and related advertisements on a network and a calendar 745 of everyday activities for selecting a related time interval. Items indicated by the hyperlink 740 can be selected on the basis of information that could have been known from an individual in an investigation and an achievement determined by the health index.

The category of "vitality degree" of the health index 555 is designed to enable the user to monitor recognition concerning whether the user was fine in a specific day and is based on essentially subjective grade information directly input by the user. The user performs ranking desirably using scales 1 to 5 concerning the following nine areas, i.e., (1) mental sharpness, (2) mental and psychological happiness degrees, (3) an energy level, (4) an ability to cope with stress of life, (5) a degree of putting importance on a reputation, (6) a physical happiness degree, (7) self-constraint, (8) a motivation, and (9) a comfort through a relation with others. These degrees (ranks) are averaged and used for calculation of the bar graph of the health index 555.

FIG. 20 shows a vitality degree Web page 750. The vitality degree Web page 750 enables the user to check vitality degrees over a time interval selectable by the user including continuous or discontinuous any days. Note that, in an example shown in FIG. 20, the vitality degrees are displayed as health indexes. On the vitality degree Web page 750, by using a selection box 760 of the vitality degrees, the user can perform selection for checking bar graph 755 of the vitality degree concerning one category or arrange bar graphs 755 of the vitality degrees side by side and compare the bar graphs 755 concerning two categories or two or more categories. For example, the user sometimes desires to set only a bar graph of sleep in an active state in order to check whether a general rank of sleep is improved compared with the last month or sometimes simultaneously displays sleep and activity levels to thereby compare and evaluate a grade of sleep and a grade of an activity level corresponding to the grade of sleep and check whether some correlation is present between the days. The user sometimes displays a grade of nutrition and a grade of a vitality degree concerning a predetermined time interval and checks whether some correlation is present between an everyday meal habit and a meal habit and a vitality degree during the interval. FIG. 20 shows, as an example for explanation, comparison of sleep and activity levels in a week of June 8 to June 14 by bar graphs. The vitality degree Web page 750 also includes a track calculator 765 that displays access information such as a total number of days in which the user logged in and used the health manager, and a ratio of days in which the user used the health manager after becoming a member, and a ratio of time in which the user used the sensor device in order collect data, and statistics.

An example of the Web page 550 serving as a start point of the health manager shown in FIG. 14 includes summaries 556a to 556f of a plurality of categories selectable by the user respectively corresponding to the categories of the health index 555 serving as health degrees. The summaries 556a to 556f of the categories present subsets of data selected and filtered in advance concerning the corresponding categories. The summary 556a of the nutrition category indicates a target value and an actual value of every day of a calorie intake amount. The summary 556b of the activity level category indicates a target value and an actual value of every day of a burned calorie amount. The summary 556c of the mental concentration indicates a target value and an actual value of the depth of mental concentration. The summary 556d of the sleep category indicates a target sleep time, an actual sleep time, and a grade of the quality of sleep. The summary 556e of the everyday activity category indicates a target point and an actual point based on a ratio of completed activities to recommended healthy daily routines (everyday activities). The summary 556f of the vitality degree category indicates a target grade and an actual grade of a health degree in the day.

The Web page 550 can also include a hyperlink (not shown in the figure) to news articles, a comment (not shown in the figure) to the user based on a tendency such as undernourishment checked by a first investigation, and a sign (not shown in the figure). The Web page 550 can also include an everyday routine portion 557 for providing the user with information every day. As a comment of the everyday routine portion 557, for example, a water intake needed every day and an advice of specific means for enabling the water intake can be displayed. The Web page 550 can include a problem solution section 558 for actively evaluating the achievement of the user in the categories of the health index 555 and presenting an advice for improvement. For example, when a system indicates that a sleep level of the user is "low" and the user has insomnia, the problem solution section 558 can advise a method for improving sleep. The problem solution section 558 can include a question of the user concerning improvement of achievement. The Web page 550 can include an everyday data section 559 for starting a dialog box. With the dialog box, the user can easily perform an input of various data required by the health manager. As it is known in the technical field, it is possible to select whether the input of the data is an input of a list presented in advance or an input in a normal free text format. The Web page 550 can include a body state section 561 for giving information concerning a life symptom such as height, weight, body measurement values, a BMI, and a heart rate, a blood pressure or any physiological parameters of the user.

The embodiments of the invention devised by the inventor are specifically explained above. However, the invention is not limited to the embodiments explained above. It is possible to add various changes without departing from the spirit of the invention.

For example, in the embodiments and the modifications, the biological information measuring devices 1, 201A, 201B, 201C, 301, 401, and 501 of the wrist device (wristable device) type such as the wristwatch worn on the wrist of the user are explained. The biological information measuring device is not limited to this type and may be a type worn on some part of the upper limb further on the trunk side than the wrist, some part of the lower limb including the ankle, or the neck.

In the embodiments and the modifications, the biological information measuring device mounted with the pulse wave sensor (the pulse-wave sensor section 5), the acceleration sensor 131, the angular velocity sensor 132, the atmospheric pressure sensor 140, the temperature sensor 160, and the GPS unit 170 as the detecting sections is explained. However, the biological information measuring device is not limited to this. For example, the biological information measuring device may be mounted with sensors (detecting sections) that measure physiological parameters such as a heart rate, a blood pressure, an expiration amount, skin conductivity, and skin humidity.

What is claimed is:

1. A biological information measuring device comprising:
   a case section having, in sectional view, a trapezoidal shape including an upper base and a lower base shorter than the upper base, a first leg crossing the upper base and the lower base, and a second leg that is an opposite side of the first leg;
   a display section disposed on the second leg side;
   a circuit board housed in the case section;
   a flexible board configured to electrically connect the circuit board and the display section;
   a pulse wave sensor disposed on the first leg side and configured to detect a pulse wave signal of a user; and
   a vibration motor housed on the first leg side in the case section in sectional view,
   wherein the vibration motor is disposed further on the upper base side than a center of a surface on the first leg side.

2. The biological information measuring device according to claim 1,
   wherein the first leg and the upper and lower bases cross substantially orthogonally.

3. The biological information measuring device according to claim 1,
   wherein the upper base and the lower base are disposed in parallel.

4. The biological information measuring device according to claim 1,
   wherein the pulse wave sensor is disposed in a region including a center of gravity of the case section on a surface of the case section on the first leg side.

5. The biological information measuring device according to claim 1,
   wherein the pulse wave sensor is provided on a surface of the case section on the first leg side and disposed in a sensor projecting section projecting to a body side of the user.

6. The biological information measuring device according to claim 1, further comprising
   at least one battery housed in the case section, wherein the battery is disposed with a center of gravity of the battery located further on the upper base side than a center of a surface on the first leg side.

7. The biological information measuring device according to claim 1, further comprising a band section configured to fix the case section to an organism, wherein the band section includes a first band connected to the upper base side, a second band connected to the lower base side, and a connecting section that connects the first band and the second band.

8. The biological information measuring device according to claim 7, wherein surfaces of the first band and the second band on the organism side and a surface of the case section on the first leg side form a continuous surface.

9. The biological information measuring device according to claim 1, wherein a surface of the case section on the first leg side has a curved surface.

10. The biological information measuring device according to claim 1, wherein an atmospheric pressure sensor configured to detect an atmospheric pressure is housed in the case section, and the atmospheric pressure sensor is disposed not to overlap the pulse wave sensor in plan view.

11. The biological information measuring device according to claim 10, wherein the atmospheric pressure sensor and the pulse wave sensor are respectively disposed on different surfaces of the circuit board.

12. The biological information measuring device according to claim 10, wherein the circuit board includes a main circuit board mounted with at least the atmospheric pressure sensor and a sensor circuit board separate from the main circuit board and mounted with the pulse wave sensor.

13. The biological information measuring device according to claim 10, wherein a hole section that causes the atmospheric pressure sensor and external air to communicate with each other is provided in a region in an extending direction to the second leg side of the sensor projecting section of the case section.

14. The biological information measuring device according to claim 5, wherein the vibration motor is mounted on a surface of the circuit board on a same side as the pulse wave sensor.

15. The biological information measuring device according to claim 1, further comprising a temperature sensor housed in the case section and configured to detect temperature of an organism, wherein the temperature sensor is mounted on a surface of the circuit board on a same side as the pulse wave sensor.

16. The biological information measuring device according to claim 1, wherein the case section houses a position calculating section configured to calculate position information on the basis of a positioning signal from a positioning satellite and a first antenna configured to acquire the positioning signal, and the first antenna is disposed on the lower base side.

17. The biological information measuring device according to claim 13, wherein the case section houses a second antenna configured to communicate biological information with an external device, and the second antenna is disposed on the lower base side in sectional view.

18. The biological information measuring device according to claim 17, wherein at least one of the first antenna and the second antenna is disposed in a vicinity of the hole section.

19. The biological information measuring device according to claim 1, wherein an inertial sensor or an inertial sensor section including a plurality of kinds of the inertial sensors is provided in the case section, and the inertial sensor or the inertial sensor section is disposed in a region including a center of gravity of the case section in plan view.

20. The biological information measuring device according to claim 19, wherein the inertial sensor is disposed not to overlap the vibration motor in plan view.

21. The biological information measuring device according to claim 1, wherein the pulse wave sensor is a photoelectric pulse wave sensor including a light source configured to irradiate light on a body of the user and a light receiving element configured to receive reflected light from the body of the user, a light blocking member is disposed between the pulse wave sensor and a surface that is in contact with the organism, and a first optical waveguide configured to optically connect the light source and the surface that is in contact with the organism and a second optical waveguide configured to optically connect the light receiving element and the surface that is in contact with the organism are provided in the light blocking member.

* * * * *